(12) United States Patent
Ando et al.

(10) Patent No.: US 8,553,733 B2
(45) Date of Patent: Oct. 8, 2013

(54) LIGHT SOURCE DEVICE, OBSERVATION DEVICE, AND PROCESSING DEVICE

(75) Inventors: Taro Ando, Hamamatsu (JP); Yoshiyuki Ohtake, Hamamatsu (JP); Naoya Matsumoto, Hamamatsu (JP); Takashi Inoue, Hamamatsu (JP); Haruyoshi Toyoda, Hamamatsu (JP); Norihiro Fukuchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 372 days.

(21) Appl. No.: 12/527,618

(22) PCT Filed: Feb. 21, 2008

(86) PCT No.: PCT/JP2008/052971
§ 371 (c)(1),
(2), (4) Date: Dec. 9, 2009

(87) PCT Pub. No.: WO2008/105312
PCT Pub. Date: Sep. 4, 2008

(65) Prior Publication Data
US 2010/0103962 A1 Apr. 29, 2010

(30) Foreign Application Priority Data

Feb. 26, 2007 (JP) ................................ P2007-045888
Mar. 23, 2007 (JP) ................................ P2007-077579

(51) Int. Cl.
*H01S 3/10* (2006.01)
(52) U.S. Cl.
USPC ............... 372/20; 372/50.1; 372/55; 359/238
(58) Field of Classification Search
USPC ........................................................ 372/20
See application file for complete search history.

(56) References Cited

U.S. PATENT DOCUMENTS

| 4,952,010 A | * | 8/1990 | Healey et al. ................... 359/11 |
| 5,214,531 A | * | 5/1993 | Torii et al. ................... 359/223.1 |

(Continued)

FOREIGN PATENT DOCUMENTS

| DE | 691 16 485 | 6/1996 |
| EP | 0 476 931 | 3/1992 |

(Continued)

OTHER PUBLICATIONS

J. Arlt et al., "The production of multiringed Laguerre-Gaussian modes by computer-generated holograms," Journal of Modern Optics, 1998, vol. 45, No. 6, pp. 1231-1237.

(Continued)

*Primary Examiner* — Xinning Niu
(74) *Attorney, Agent, or Firm* — Drinker Biddle & Reath LLP

(57) ABSTRACT

A light source device 1 includes a laser light source 10 and an optical phase modulator 15 or the like. The optical phase modulator 15 inputs coherent light output from the laser light source 10 and transmitted through a beam splitter 14, phase-modulates the light according to the position on a beam cross section of the light, and outputs the phase-modulated light to the beam splitter 14. When (p+1) areas sectioned by p circumferences centered on a predetermined position are set on a beam cross section of light input to the optical phase modulator 15, the more outside each of the (p+1) areas is, the wider the radial width of the area, the amount of phase modulation is constant in each of the (p+1) areas, and the amounts of phase modulation differ by $\pi$ between two adjacent areas out of the (p+1) areas.

4 Claims, 20 Drawing Sheets

(56) References Cited

U.S. PATENT DOCUMENTS

| | | |
|---|---|---|
| 5,477,554 A | 12/1995 | Yoshii et al. |
| 2001/0045529 A1* | 11/2001 | Iketaki et al. ............. 250/493.1 |
| 2002/0141472 A1 | 10/2002 | Koyama et al. |
| 2004/0219699 A1 | 11/2004 | Koyama et al. |
| 2007/0081233 A1* | 4/2007 | Hattori ........................ 359/385 |

FOREIGN PATENT DOCUMENTS

| | | |
|---|---|---|
| EP | 0476931 A2 * | 3/1992 |
| JP | 4-123017 | 4/1992 |
| JP | 2002-098930 | 4/2002 |
| JP | 2002-359432 | 12/2002 |
| JP | 2005-144524 | 6/2005 |

OTHER PUBLICATIONS

D. Grier, "A revolution in optical manipulation," Nature, Aug. 14, 2003, vol. 424, pp. 810-816.

M. W. Beijersbergen et al., "Helical-wavefront laser beams produced with a spiral phaseplate," Optics Communications, 1994, vol. 112, pp. 321-327.

K. Sueda et al., "Laguerre-Gaussian beam generated with a multi-level spiral phase plate for high intensity laser pulses," Optics Express, Jul. 26, 2004, vol. 12, No. 15, pp. 3548-3553.

N.R. Heckenberg et al., "Generation of optical phase singularities by computer-generated holograms," Optical Letters, Feb. 1, 1992, vol. 17, No. 3, pp. 221-223.

N.R. Heckenberg et al., "Laser beams with phase singularities," Optical and Quantum Electronics, 1992, vol. 24, pp. S951-5962.

K.S. Youngworth et al., "Focusing of high numerical aperture cylindrical-vector beams," Optics Express, Jul. 17, 2000, vol. 7, No. 2, pp. 77-87.

R. Oron et al., "The formation of laser beams with pure azimuthal or radial polarization," Applied Physics Letters, Nov. 20, 2000, vol. 77, No. 21, pp. 3322-3324.

* cited by examiner (a)

(b)

(a)

(b)

ical FIELD

LIGHT SOURCE DEVICE, OBSERVATION DEVICE, AND PROCESSING DEVICE

TECHNICAL FIELD

The present invention relates to a light source device for generating light having a predetermined phase distribution on a beam cross section of light, and an observing device and a processing device using the same.

BACKGROUND ART

In the case of observing an subject or processing a workpiece, light output from a light source such as a laser light source is focused and irradiated onto the subject or workpiece through an irradiating optical system including lenses etc. It is known that the beam waist diameter being a measure of the size of the focusing diameter when thus focused light can be reduced only to about a half of the wavelength of light. This is referred to as a diffraction limit. However, the diffraction limit is a matter in terms of Gaussian mode (or fundamental mode) light. On the other hand, the existence of high-order mode lights having more minute spatial structures than the diffraction limit is known.

Known as light beams having such properties are Bessel beams, Laguerre-Gaussian beams (hereinafter, referred to as "LG beams"), and polarization mode beams. Using such light beams allows effectively focusing the energy of light into a minute area smaller than the diffraction limit. In the past, there have been proposed, on the basis of this principle, inventions such as pickup devices, micro-processing technologies, and microscopes having resolutions smaller than the diffraction limit using Bessel beams.

Moreover, light source devices that output LG beams have been described in, for example, Non-Patent Documents 1 to 6. The light source devices described in these documents generate LG beams whose phases change along the circumferential direction in light beam cross sections. Such LG beams are expected to be applied to optical tweezers, quantum computations and quantum communications, etc., and have currently been attracting attention in the optical and physical fields.

Non-Patent Document 1: J. Arlt, et al., Journal of Modern Optics, Vol. 45, No. 6, pp. 1231-1237 (1998).
Non-Patent Document 2: D. G Grier, Nature, Vol. 424, pp. 810-816 (2003).
Non-Patent Document 3: M. W. Beijersbergen, et al., Optics communications, Vol. 112, pp. 321-327 (1994).
Non-Patent Document 4: K. Sueda, et al., Optics Express, Vol. 12, No. 15, pp. 3548-3553 (2004).
Non-Patent Document 5: N. R Heckenberg, et al., Optics Letters, Vol. 17, No. 3, pp. 221-223 (1992).
Non-Patent Document 6: N. R. Heckenberg, et al., Optical and Quantum Electronics, Vol. 24, No. 24, pp. 155-166 (1992).
Non-Patent Document 7: K. S. Youngworth and T. G Brown, Optics Express, Vol. 7, No. 2, pp. 77-87 (2000).
Non-Patent Document 8: R. Oron, et al., Applied Physics Letters, Vol. 77, No. 21, pp. 3322-3324 (2000).

DISCLOSURE OF THE INVENTION

Problem to be Solved by the Invention

Conventionally, there have been known several light beams whose central spot diameters when being focused are smaller than the diffraction limit, however, all of the beams have had problems such that a complicated optical system is necessary for generation, or the generated beam is low quality. In particular, Bessel beams are light beams having properties most similar to those of LG beams, however, currently known generating techniques can only generate approximate Bessel beams. Further, even the conventional techniques for generating approximate Bessel beams are associated with difficulties in optical techniques. More specifically, an axicon is necessary to generate approximate Bessel beams and the axicon has difficulty in obtaining a highly accurate element and adjusting an optical axis in use, and therefore, a great technological burden is required for generating approximate Bessel beams of a sufficient quality for the purpose mentioned above.

It is an object of the present invention to provide a light source device that is capable of outputting light having super-resolution characteristics of the same level as those of Bessel beams and having features such as focusing characteristics and ease in generation. It is also an object of the present invention to provide an observing device that allows observing a subject at high resolution using such a light source device and a processing device that allows processing a workpiece at high resolution using such a light source device.

Means for Solving the Problem

A light source device according to the present invention includes (1) a light source for outputting coherent light, and (2) an optical phase modulator for inputting the light output from the light source, phase-modulating the light according to a position on a beam cross section of the light, and outputting the phase-modulated light. Further, in the light source device according to the present invention, when (p+1) areas sectioned by p circumferences centered on a predetermined position are set on a beam cross section of the light input to the optical phase modulator, the more outside each of the (p+1) areas is, the wider the radial width of the area, an amount of phase modulation is constant in each of the (p+1) areas, and the amounts of phase modulation differ by $\pi$ between two adjacent areas out of the (p+1) areas. Where p is a natural number.

Moreover, a light source device according to the present invention includes (1) a light source for outputting coherent light, and (2) an optical phase modulator for inputting the light output from the light source, phase-modulating the light according to a position on a beam cross section of the light, and outputting the phase-modulated light, wherein an amount of phase modulation in each pixel is set based on an externally input control signal for the optical phase modulator. Further, in the light source device according to the present invention, when (p+1) areas sectioned by p circumferences centered on a predetermined position are set on a beam cross section of the light input to the optical phase modulator, the more outside each of the (p+1) areas is, the wider the radial width of the area, the amount of phase modulation is constant in each of the (p+1) areas, and the amounts of phase modulation differ by $\pi$ between two adjacent areas out of the (p+1) areas. Where p is a natural number.

Also, an arbitrary phase $\alpha$ and a phase $(\alpha+2n\pi)$ are mutually equivalent when n is an integer, and it suffices for distribution of the amount of phase adjustment to be concerned only with relative values while ignoring offset values. In consideration of these, the amount of phase modulation in the optical phase modulator can be limited to a range from the phase $\alpha$ to the phase $(\alpha+2n\pi)$, and $\alpha$ may be provided as a value 0.

Moreover, an observing device according to the present invention is a device for observing an subject, and comprises the light source device according to the present invention mentioned above, an irradiating optical system for focusing and irradiating light output from the light source device onto an observation spot within the subject, a scanning unit for scanning the observation spot within the subject, and a detecting optical system for detecting light generated as a result of focusing and irradiating light onto the observation spot by the irradiating optical system.

Moreover, a processing device according to the present invention is a device for processing an workpiece, and comprises the light source device according to the present invention mentioned above, an irradiating optical system for focusing and irradiating light output from the light source device onto the processing spot within the workpiece, and a scanning unit for scanning the processing spot within the workpiece.

Moreover, a light source device according to the present invention includes (1) a surface-emitting laser element for outputting laser light from an exit surface, the surface-emitting laser element having a resonator for causing laser oscillation, and (2) an optical phase-modulation unit for phase-modulating input light according to a position on a beam cross section of the light, and outputting the phase-modulated light, wherein the optical phase-modulation unit is provided on the exit surface of the surface-emitting laser element or in the resonator. Further, in the light source device according to the present invention, when (p+1) areas sectioned by p circumferences centered on a predetermined position are set on a beam cross section of the light input to the optical phase-modulation unit, the more outside each of the (p+1) areas is, the wider the radial width of the area, an amount of phase modulation is constant in each of the (p+1) areas, and the amounts of phase modulation differ by $\pi$ between two adjacent areas out of the (p+1) areas. Where p is a natural number.

In the above-mentioned light source device, it is preferable that the exit surface of the surface-emitting laser element is processed to form the optical phase modulating unit, and it is also preferable that the separately formed optical phase modulating unit is fixed to the exit surface of the surface-emitting laser element.

Effects of the Invention

A light source device according to the present invention is capable of outputting light having super-resolution characteristics of the same level as those of Bessel beams and having features such as focusing characteristics and ease in generation. Moreover, using the light source device allows observing an subject at high resolution, and allows processing a workpiece at high resolution.

Figure 1:
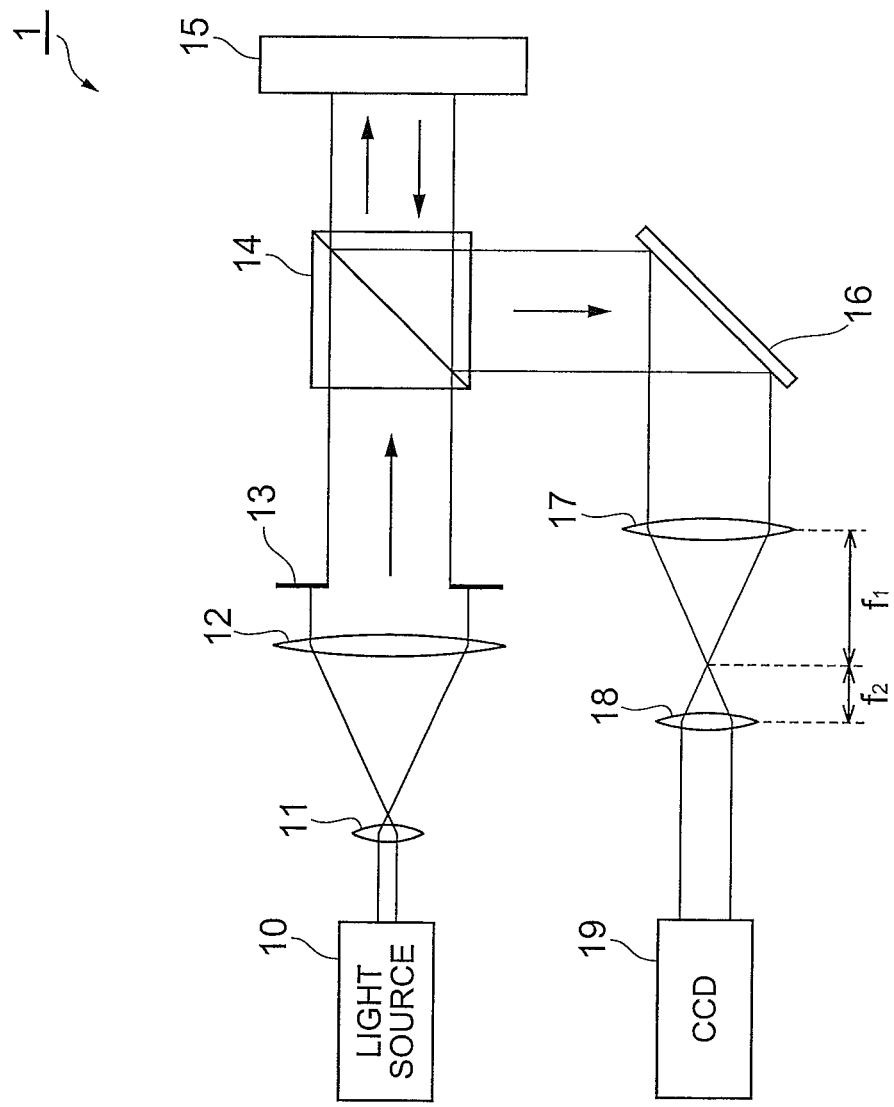
FIG. 1 A configuration diagram of a light source device 1 according to a first embodiment.

DESCRIPTION OF REFERENCE NUMERALS 1, 2 . . . Light source device, 3 . . . Observing device, 4 . . . Processing device, 8 . . . Subject, 9 . . . Workpiece, 10 . . . Laser light source, 11, 12 . . . Convex lens, 13 . . . Aperture, 14 . . . Beam splitter, 15 . . . Optical phase modulator, 16 . . . Mirror, 17, 18 . . . Convex lens, 19 . . . CCD camera, 20 . . . Optical phase modulator, 21 . . . Mirror, 30 . . . Mirror, 31 . . . Beam splitter, 32 . . . Objective lens, 33 . . . Filter, 34 . . . Photodetector, 35 . . . Control unit, 36 . . . Display unit, 37 . . . Moving stage, 101 to 103 . . . Light source device, 110 . . . Surface-emitting laser element, 111 . . . Substrate, 112 . . . DBR layer, 113 . . . Cladding layer, 114 . . . Core layer, 115 . . . Active layer, 116 . . . Core layer, 117 . . . Cladding layer, 118 . . . DBR layer, 120 . . . Optical phase-modulation unit, 121 . . . First medium, 122 . . . Second medium, 130 . . . Surface-emitting laser element, 131 . . . Substrate, 132 . . . DBR layer, 133 . . . Cladding layer, 134 . . . Core layer, 135 . . . Active layer, 136 . . . Core layer, 137 . . . Cladding layer, 138 . . . DBR layer, 140 . . . Optical phase-modulation unit, 141 . . . First medium, 142 . . . Second medium, 150 . . . Surface-emitting laser element, 151 . . . Substrate, 152 . . . DBR layer, 153 . . . Cladding layer, 154 . . . Core layer, 155 . . . Active layer, 156 . . . Core layer, 157 . . . Cladding layer, 158 . . . DBR layer, 160 . . . Optical phase-modulation unit, 161 . . . First medium, 162 . . . Second medium, 170 . . . Reflective optical phase-modulation unit, 171 . . . First medium, 172 . . . Second medium, 180 . . . Reflective optical phase-modulation unit, 181 . . . First medium, 182 . . . Second medium, 191 . . . P-electrode, 192 . . . N-electrode.

BEST MODES FOR CARRYING OUT THE INVENTION

Hereinafter, the best modes for carrying out the present invention will be described in detail with reference to the accompanying drawings. Here, in the description of the drawings, identical elements are designated by identical reference numerals so as to avoid overlapping descriptions.

First, description will be given of a first embodiment of a light source device according to the present invention. FIG. 1 is a configuration diagram of a light source device 1 according to the present embodiment. The light source device 1 shown in this figure includes a laser light source 10, a convex lens 11, a convex lens 12, an aperture 13, a beam splitter 14, a reflective optical phase modulator 15, a mirror 16, a convex lens 17, and a convex lens 18. Also shown in this figure is a CCD camera 19 for observing the intensity distribution in a beam cross section of light output from the convex lens 18.

The laser light source 10, which is for outputting coherent laser light, is for example a He—Ne laser light source or the like. The lens 11 and the lens 12, which act as a beam expander, input light output from the laser light source 10 to expand the light in beam diameter and output the light as a parallel light. The aperture 13 has a circular opening, inputs light output from the lens 11 and the lens 12, and outputs, out of a beam cross section of the light, a part that passes through the opening. The beam splitter 14 transmits a part of the light propagated from the aperture 13 and outputs the same to the optical phase modulator 15, and reflects a part of the light propagated from the optical phase modulator 15 and outputs the same to the mirror 16.

The optical phase modulator 15 inputs light output from the laser light source 10 and transmitted through the beam splitter 14, phase-modulates the light according to the position on a beam cross section of the light, and reflects the phase-modulated light to the beam splitter 14. The optical phase modulator 15 is, for example, a device (SLM: Spatial Light Modulator) for which the amount of phase modulation at each pixel when reflecting light is set based on an externally input control signal. When an SLM is used as the optical phase modulator 15, it is possible to electrically write a spatial distribution of the amount of phase modulation, which allows providing various phase modulation distributions according to necessity.

The mirror 16 reflects light propagated from beam splitter 14, and outputs the reflected light to the lens 17. The lens 17 and the lens 18 input light reflected by the mirror 16, adjust the light in beam diameter, and output the adjusted light as a parallel light. The CCD camera 19 inputs light output from the lens 17 and the lens 18, and detects a light intensity distribution in a beam cross section of the light.

In the light source device 1, coherent laser light output from the laser light source 10 is expanded in beam diameter by the convex lens 11 and the convex lens 12, and then partly passes through the circular opening of the aperture 13 in the beam cross section of the laser light so that the beam cross section becomes circular, and is further transmitted through the beam splitter 14 and input to the optical phase modulator 15. Light input to the optical phase modulator 15 undergoes phase modulation by the optical phase modulator 15 according to the position on the beam cross section and to be reflected. The light phase-modulated and reflected by the optical phase modulator 15 is reflected by the beam splitter 14, further reflected by the mirror 16, adjusted in beam diameter by the convex lens 17 and the convex lens 18, and made incident into a light receiving surface of the CCD camera 19, and a light intensity distribution in the light beam cross section is detected by the CCD camera 19.

Figure 2:
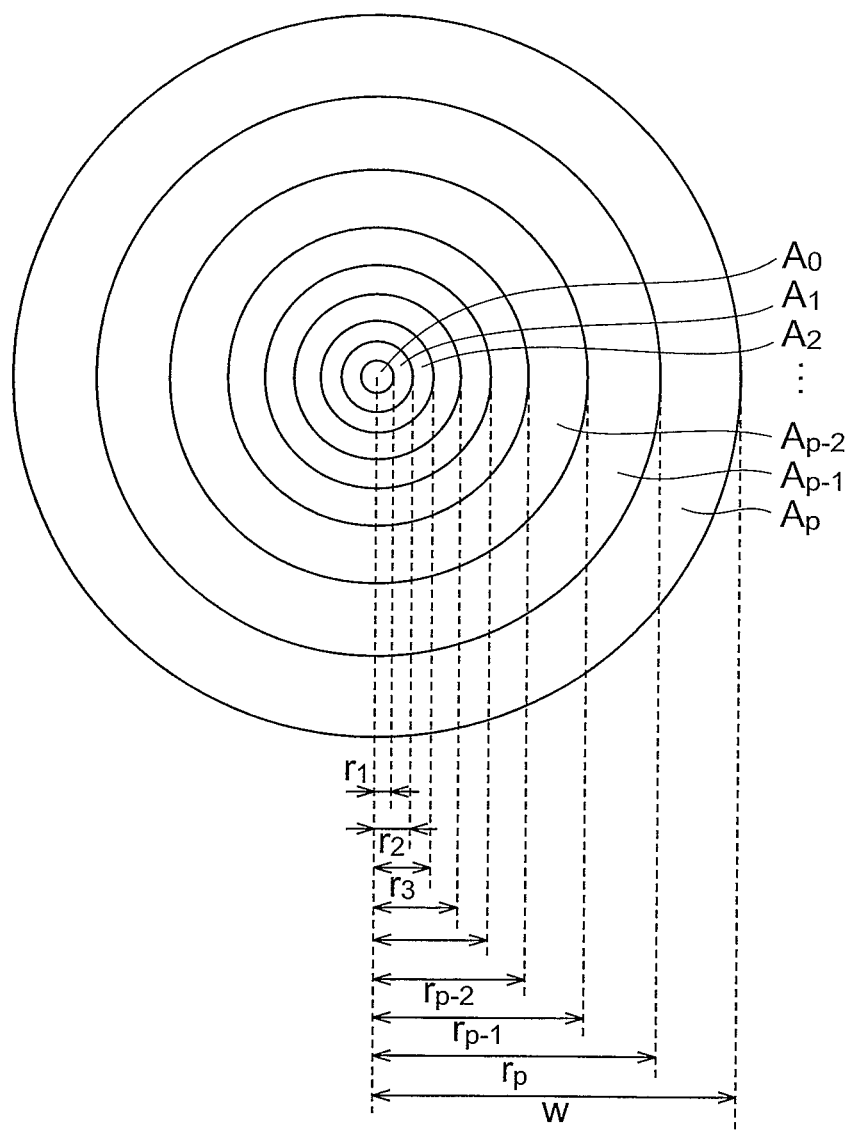
FIG. 2 A view explaining phase modulation in a spatial light modulator 15.

The amount of phase modulation to be provided to reflected light in the optical phase modulator 15 will be described in greater detail as follows. As shown in FIG. 2, (p+1) areas $A_0$ to $A_p$ sectioned by p respective circumferences with radii $r_1$ to $r_p$ centered on a predetermined position are set on a beam cross section of light input to the optical phase modulator 15. The areas are provided in order from inside as $A_0, A_1, A_2, \ldots, A_p$. The area $A_0$ is an area inside the circumference with a radius $r_1$. The area $A_i$ is an area between the circumference with a radius $r_i$ and the circumference with a radius $r_{i+1}$ (i=1, 2, 3, ..., p−1). The area $A_p$ is an area outside the circumference with a radius $r_p$ and within a light beam (waist radius w).

At this time, the more outside each of the (p+1) areas $A_0$ to $A_p$ is, the wider the radial width of the area. More specifically, the following relational expression holds true between the radii $r_1$ to $r_p$. In addition, the area $A_0$ located at the innermost side has the radius $r_1$ as a radial width thereof.

[Numerical Expression 1]

$$w - r_p > r_p - r_{p-1} > r_{p-1} - r_{p-2} > \ldots > r_2 - r_1 > r_1 \quad (1)$$

Further, the amount of phase modulation is constant in each of the (p+1) areas $A_0$ to $A_p$, and the amounts of phase modulation differ by $\pi$ between two adjacent areas out of the (p+1) areas $A_0$ to $A_p$. More specifically, the amount of phase modulation $\phi_0$ in each area of the even number-th areas $A_0, A_2, A_4, \ldots$ is constant. Also, the amount of phase modulation $\phi_1$ in each area of the odd number-th areas $A_1, A_3, A_5, \ldots$ is constant. In addition, these amounts of phase modulation $\phi_0$ and $\phi_1$ mutually differ by $\pi$.

Lines of phase discontinuity expressed by the p circumferences with radii $r_1$ to $r_p$ that need to be set in terms of the radial direction r are set as follows. The line of phase discontinuity exists at a part (node) where the light intensity equals 0. In the case of an LG mode, the nodes of a light intensity distribution can be determined from zeros of Sonine polynomials. That is, the value of a variable z where a Sonine polynomial $S_p^q(z)$ defined by the following expression (2) takes a value 0 is determined. Here, p, which is referred to as a radial exponent, is a non-negative integer number. In addition, q, which is referred to as an azimuthal exponent, is an arbitrary integer number other than 0.

[Numercial Expression 2]

$$S_p^q(z) = \sum_{k=0}^{p} \frac{(-1)^k \cdot (p+|q|)!}{(p-k)! \cdot (|q|+k)! \cdot k!} \cdot z^k \quad (2)$$

In particular, the azimuthal exponent q is provided as a value 0 in the present embodiment. At this time, the above expression (2) results in a Laguerre polynomial expressed by the following expression (3). The Laguerre polynomial is a p-degree polynomial, which has p different positive real roots $a_1$ to $a_p$. By use of these roots $a_i$ and the light beam waist radius w, the radii $r_i$ of lines of phase discontinuity are expressed by the following expression (4) (i=1, 2, 3, ..., p).

[Numercial Expression 3]

$$S_p^{q=0}(z) = \sum_{k=0}^{p} \frac{(-1)^k \cdot p!}{(p-k)! \cdot (k!)^2} \cdot z^k \quad (3)$$

[Numerical Expression 4]

$$r_i = w\sqrt{\frac{a_i}{2}} \quad (i = 1, 2, \ldots, p) \quad (4)$$

Light reflected under such phase modulation $\phi(r)$ by the optical phase modulator 15 results in an LG beam having a radial exponent p and an azimuthal exponent 0. The LG beam, with a fixed argument variable $\theta$, has a difference in phase value of π at points pertaining to two areas that are in contact at a boundary of the line of phase discontinuity. In addition, the more outside each of the (p+1) areas $A_0$ to $A_p$ is, the wider the radial width of the area.

Figure 3:
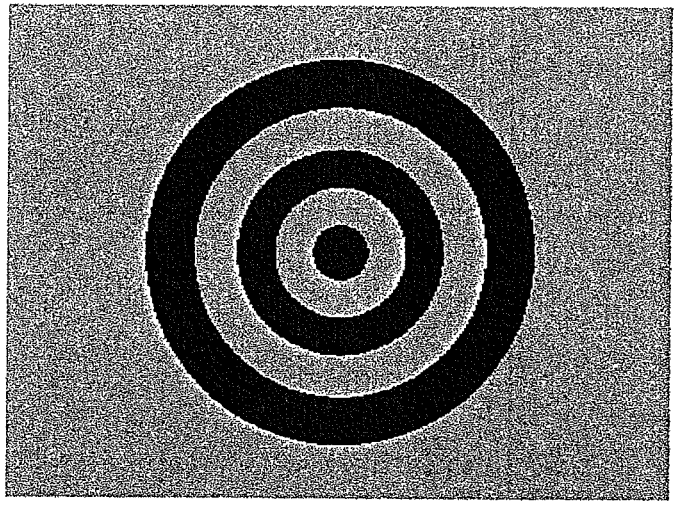
FIG. 3 A view showing distribution examples of the amount of phase modulation in the optical phase modulator 15.
Figure 3:
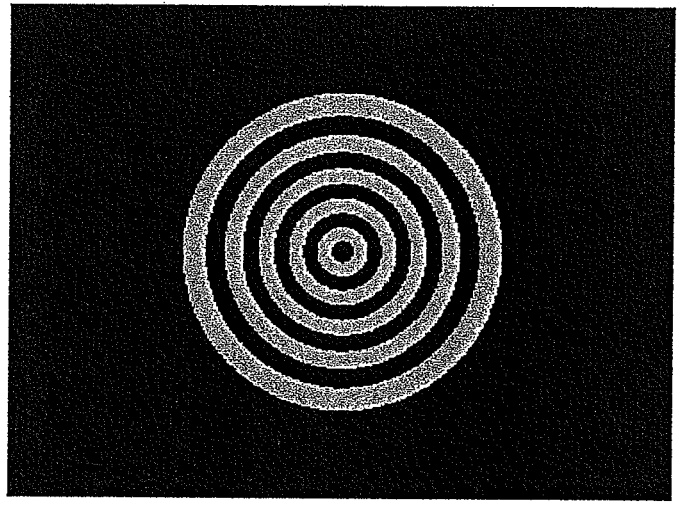

FIG. 3 is a view showing distribution examples of the amount of phase modulation in the optical phase modulator 15. FIG. 3(a) shows a distribution of the amount of phase modulation when the radial exponent p was provided as 5. In addition, FIG. 3(b) shows a distribution of the amount of phase modulation when the radial exponent p was provided as 10. In the figure, the lines of phase discontinuity have been obtained by expression (3) and expression (4) mentioned above, the amount of phase modulation is 0 in each black area, and the amount of phase modulation is π in each gray area. The more outside each area is, the wider the radial width of the area.

Figure 4:
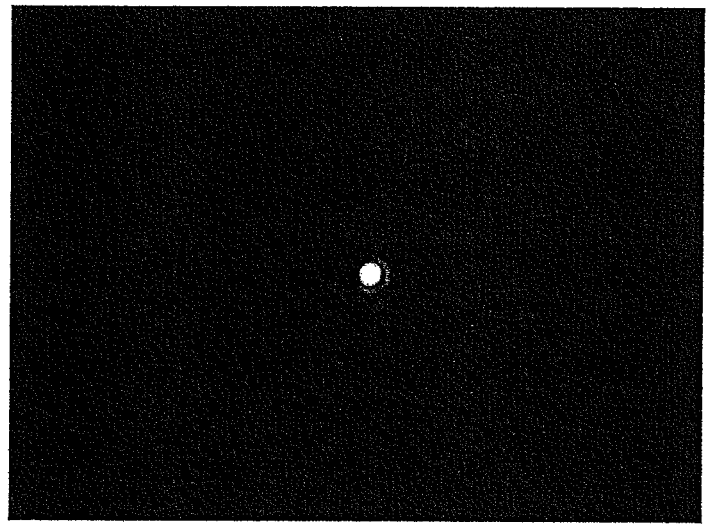
FIG. 4 A view showing the intensity distribution in a beam cross section of each of the incident light and reflected light in the optical phase modulator 15.
Figure 4:
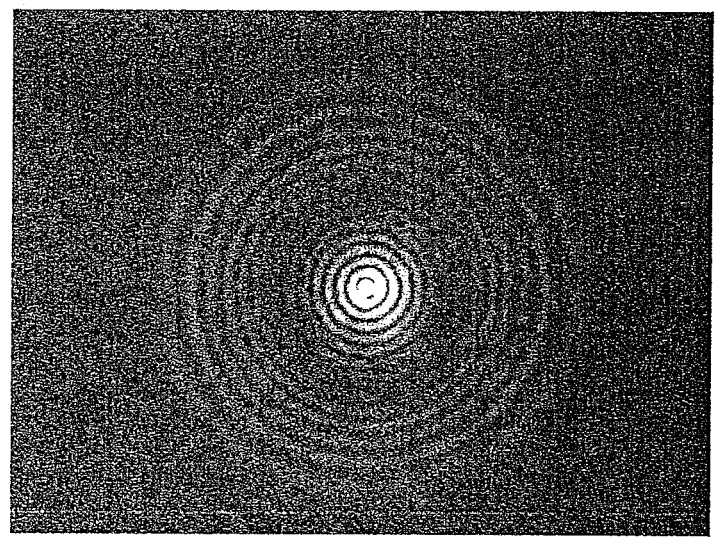

FIG. 4 is a view showing the intensity distribution in a beam cross section of each of the incident light and reflected light in the optical phase modulator 15. FIG. 4(a) shows the intensity distribution of incident light, and FIG. 4(b) shows the intensity distribution of reflected light. Here, the radial exponent p was provided as 13. More specifically, FIG. 4(b) shows the intensity distribution of an LG mode beam having a 13th-order radial exponent. In FIG. 4(b), for easy observation of a light beam sectional structure, tone correction has been performed. Accordingly, in comparison with the intensity distribution (FIG. 4(a)) of incident light, the size of a central spot ($A_0$ located at the innermost side) appears to be at the same level as that of incident light in the intensity distribution of reflected light being an LG beam (FIG. 4(b)), however, the spot is very small in actuality.

When such an LG beam having a high-order radial exponent is focused by a lens, it is impossible to reduce the beam waist diameter smaller than about a half of the wavelength (diffraction limit). However, because the internal structure of an LG mode beam is retained, the central spot (area $A_0$) of a high-order radial exponent LG mode beam has a size smaller than the diffraction limit on a focused spot.

Rings (siderobes, that is, areas $A_1$, $A_2$, $A_3$, ... ) that exist around the central spot (area $A_0$) exhibit behaviors as in a Bessel beam, and using a technique that has been established in terms of Bessel beams makes it also possible to reduce the influence thereof. As a property unique to a high-order radial exponent LG mode beam, the greater the radial exponent p is provided, the more the size of the central spot (area $A_0$) can be reduced.

In addition, expansion of the side robes (areas $A_1$, $A_2$, $A_3$, ... ) is theoretically unlimited in Bessel beams, whereas this is limited in a high-order radial exponent LG mode beam. Therefore, setting an optical system diameter so that the side robes as a whole are completely included therein allows using characteristics of the high-order radial exponent LG mode beam under more optimal conditions.

Figure 5:
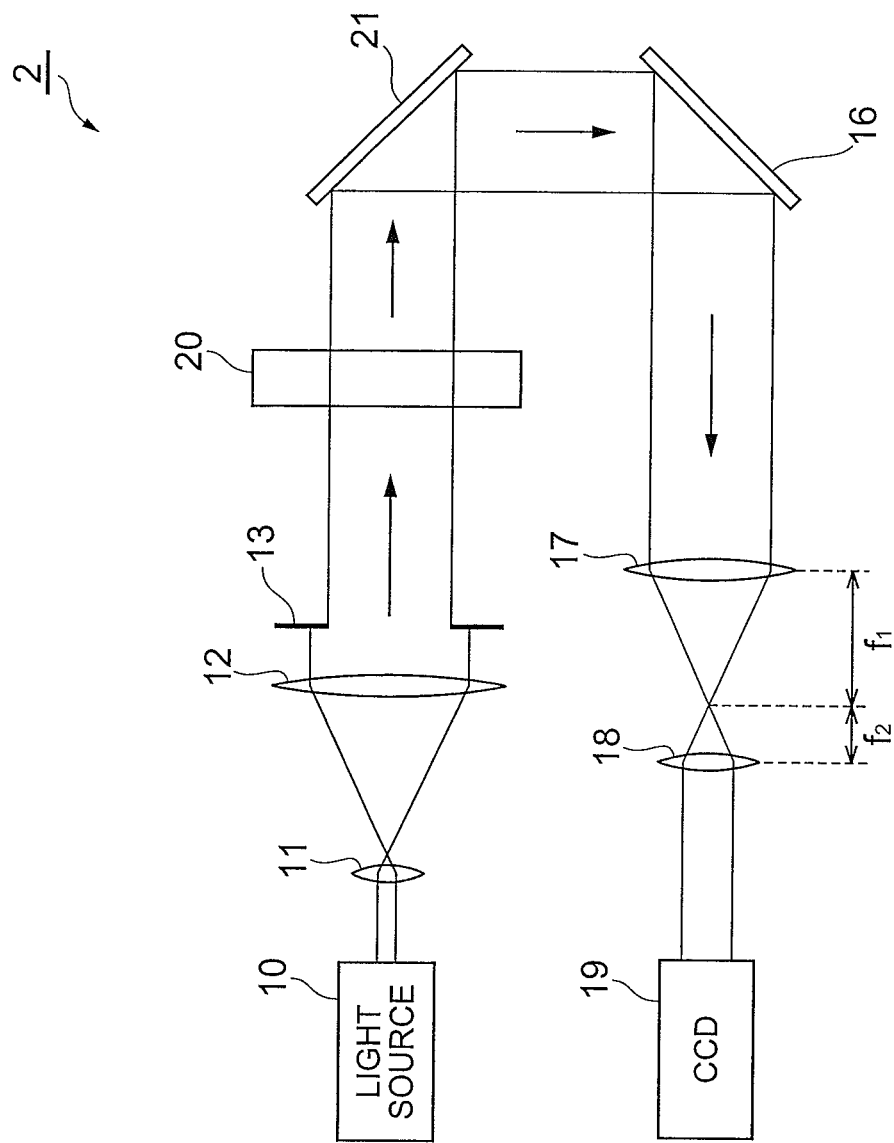
FIG. 5 A configuration diagram of a light source device 2 according to a second embodiment.

Next, description will be given of a second embodiment of a light source device according to the present invention. FIG. 5 is a configuration diagram of a light source device 2 according to the second embodiment. The light source device 2 shown in this figure includes a laser light source 10, a convex lens 11, a convex lens 12, an aperture 13, a transmissive optical phase modulator 20, a mirror 21, a mirror 16, a convex lens 17, and a convex lens 18. Also shown in this figure as well is a CCD camera 19 for observing the intensity distribution in a beam cross section of light output from the convex lens 18. In comparison with the configuration of the light source device 1 shown in FIG. 1, the light source device 2 shown in FIG. 5 differs in the point of including the transmissive optical phase modulator 20 and the mirror 21 in place of the beam splitter 14 and the reflective optical phase modulator 15.

The optical phase modulator 20 inputs light output from the laser light source 10 and passed through an opening of the aperture 13, phase-modulates the light according to the position on a beam cross section of the light, and transmits the phase-modulated light to the mirror 21. The optical phase modulator 20 is a device (SLM) for which the amount of phase modulation of each pixel when transmitting light is set based on an externally input control signal. When an SLM is used as the optical phase modulator 20, it is possible to electrically write a spatial distribution of the amount of phase modulation, which allows providing various phase modulation distributions according to necessity. The mirror 21 reflects light transmitted and output from the optical phase modulator 20 and outputs the reflected light to the mirror 16.

In the light source device 2, coherent laser light output from the laser light source 10 is expanded in beam diameter by the convex lens 11 and the convex lens 12, and then partly passes through the circular opening of the aperture 13 in the beam cross section of the laser light so that the beam cross section becomes circular, and is input to the optical phase modulator 20. Light input to the optical phase modulator 20 undergoes phase modulation by the optical phase modulator 20 according to the position on the beam cross section and to be transmitted. Light transmitted under phase modulation by the optical phase modulator 20 is reflected by the mirror 21 and the mirror 16, adjusted in beam diameter by the convex lens 17 and the convex lens 18, and made incident into a light receiving surface of the CCD camera 19, and a light intensity distribution in the light beam cross section is detected by the CCD camera 19.

The amount of phase modulation to be provided to transmitted light in the transmissive optical phase modulator 20 is the same as that to be provided to reflected light in the reflective optical phase modulator 15. More specifically, (p+1) areas $A_0$ to $A_p$ sectioned by p respective circumferences with radii $r_1$ to $r_p$ centered on a predetermined position are set on a beam cross section of light input to the optical phase modulator 20. The areas are provided in order from inside as $A_0$, $A_1$, $A_2$, ..., $A_p$. At this time, the more outside each of the (p+1) areas $A_0$ to $A_p$ is, the wider the radial width of the area. More specifically, the above expression (1) holds true between the radii $r_1$ to $r_p$. Further, the amount of phase modulation is constant in each of the (p+1) areas $A_0$ to $A_p$, and the amounts of phase modulation differ by π between two adjacent areas out of the (p+1) areas $A_0$ to $A_p$. In addition, lines of phase discontinuity expressed by the p circumferences with radii $r_1$ to $r_p$ that need to be set in terms of the radial direction r are obtained by the above-mentioned expressions (3) and (4).

Also in the light source device 2 thus configured, a distribution of the amount of phase modulation in the optical phase modulator 20 as shown in FIG. 3 is possible, and an intensity distribution in a beam cross section of each of the incident light and reflected light in the optical phase modulator 20 as shown in FIG. 4 is possible. Moreover, also in the light source device 2, the central spot (area $A_0$) of a high-order radial exponent LG beam can have a size smaller than the diffraction limit on a focused spot.

Figure 6:
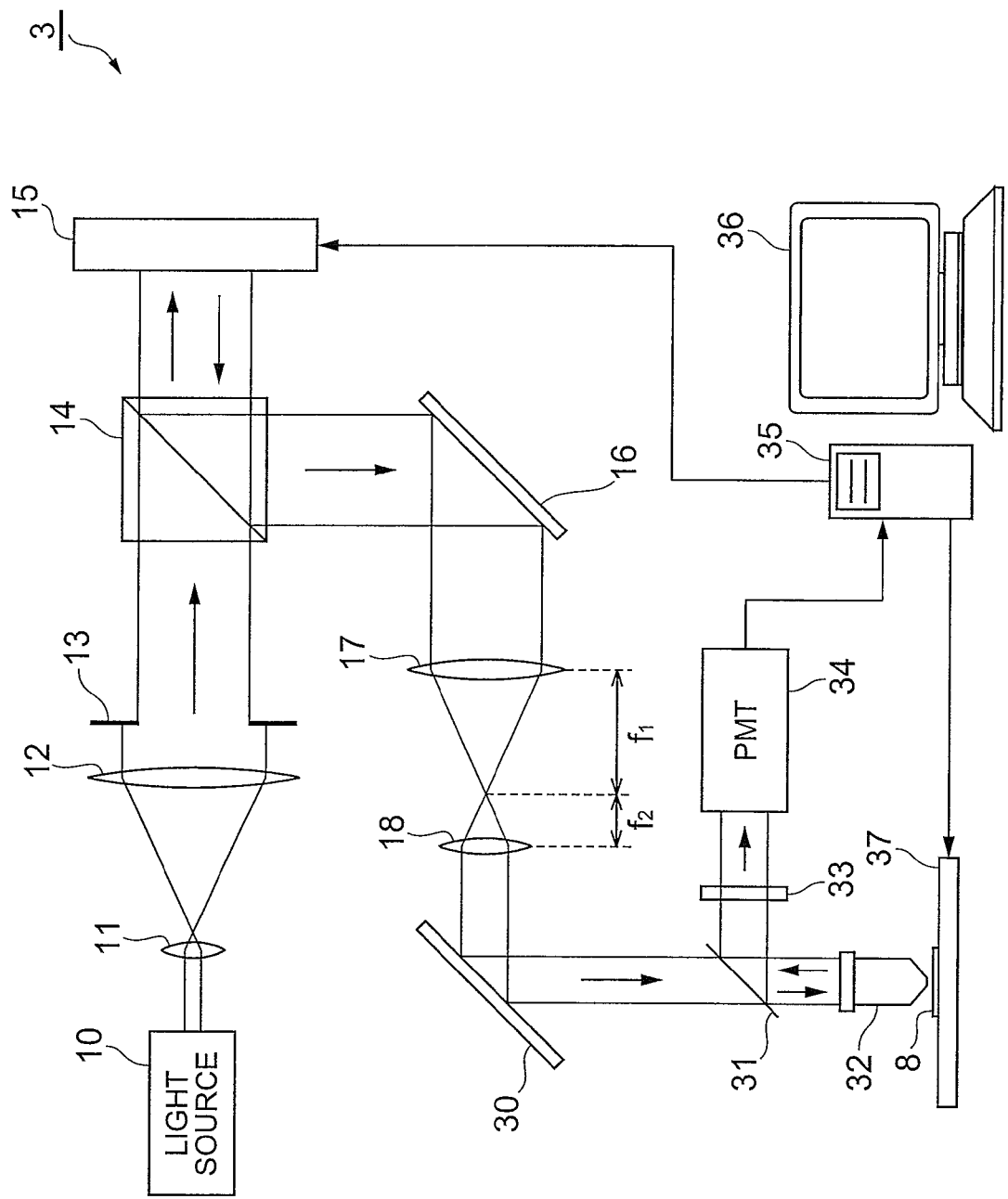
FIG. 6 A configuration diagram of an observing device 3 according to the present embodiment.

Next, description will be given of an embodiment of an observing device according to the present invention. FIG. 6 is a configuration diagram of an observing device 3 according to the present embodiment. The observing device 3 shown in this figure is a device for observing a subject 8, and further includes, as configuration elements of a scanning microscope, a mirror 30, a beam splitter 31, an objective lens 32, a filter 33, a photodetector 34, a control unit 35, a display unit 36, and a moving stage 37, besides the configuration of the light source device 1 excluding the CCD camera 19 from the configuration shown in FIG. 1.

The mirror 30 reflects light output from the lens 18, and outputs the reflected light to the beam splitter 31. The beam splitter 31 inputs light propagated from the mirror 30 and transmits the light to the objective lens 32, and inputs light propagated from the objective lens 32 and reflects the light to the filter 33. The objective lens 32 inputs light propagated from the beam splitter 31 and focuses and irradiates the light onto an observation spot of the subject 8. More specifically, the optical system from the mirror 30 through the beam splitter 31 to the objective lens 32 forms an irradiating optical system for focusing and irradiating light output from the light source device 1 onto the observation spot in the subject 8.

Moreover, the objective lens 32 inputs light generated as a result of focusing and irradiating light onto the observation spot and outputs the light to the beam splitter 31. The filter 33 inputs light propagated from the beam splitter 31 and selectively transmits light in a specific wavelength region out of the light to the photodetector 34. The photodetector 34 receives light propagated from the filter 33 and detects intensity of the light, and outputs an electrical signal of a value according to the detected received light intensity to the control unit 35. The photodetector 34 is preferably a photomultiplier tube that is capable of a highly sensitive photodetection. More specifically, the optical system from the objective lens 32 through the beam splitter 31 and the filter 33 to the photodetector 34 forms a detecting optical system for detecting light generated as a result of focusing and irradiating light onto the observation spot by the irradiating optical system.

The control unit 35 moves the moving stage 37 that carries the subject 8 to change the position of the observation spot within the subject 8. More specifically, the control unit 35 and the moving stage 37 form a scanning unit for scanning the observation spot within the subject 8.

Moreover, the control unit 35 provides the spatial light modulator 15 with a control signal for setting the amount of phase modulation of each pixel when reflecting light in the spatial light modulator 15 and thereby sets the light intensity distribution in a beam cross section of light output from the light source device 1 as described above. Further, the control unit 35 inputs an electrical signal output from the photodetector 34, and generates a two-dimensional observed image of the subject 8 from a value of the electrical signal and a position information of the observation spot within the subject 8, and displays the image by the display unit 36.

In the observing device 3, when (p+1) areas sectioned by p circumferences centered on a predetermined position are set on a beam cross section of the light output after being adjusted in beam diameter by the convex lens 17 and the convex lens 18 in the light source device 1, the more outside each of the (p+1) areas is, the wider the radial width of the area is, and the amount of phase modulation is constant in each of the (p+1) areas, and the amounts of phase modulation differ by $\pi$ between two adjacent areas out of the (p+1) areas.

Then, light output from the convex lens 18 is reflected by the mirror 30, transmitted through the beam splitter 31, and focused and irradiated onto the observation spot within the subject 8 by the objective lens 32. Light (scattered light, fluorescence, and the like) generated at the observation spot as a result of the focusing and irradiating light is reflected by the beam splitter 31 through the objective lens 32, transmitted through the filter 33, and received by the photodetector 34. The received light intensity is output as an electrical signal from the photodetector 34.

Moreover, the position (observation spot) of focusing and irradiating light from the objective lens 32 onto the subject 8 is scanned by the control unit 35 and the moving stage 37. By the scanning, light generated at each position in the subject 8 is received by the photodetector 34. Then, a two-dimensional observed image of the subject 8 is generated by the control unit 35 from the value of an electrical signal output from the photodetector 34 and a position information of the observation spot within the subject 8. The image is displayed by the display unit 36.

As described above, when an LG beam having a high-order radial exponent output from the light source device 1 is focused by the objective lens 32, it is impossible to reduce the overall beam diameter smaller than about a half of the wavelength, however, the internal structure of an LG mode beam is retained. Accordingly, in the observing device 3, the focused spot (observation spot) by the objective lens 32, that is, the central spot (area $A_0$) of an LG mode beam has a size smaller than the diffraction limit. Therefore, providing a scanning step of the subject 8 by the moving stage 37 smaller than the size of the central spot (area $A_0$) of an LG mode beam when being irradiated onto the subject 8 allows observing the subject 8 at a very high resolution. It is desirable to drive the moving stage 37 by use of a piezo actuator or the like.

In addition, the observing device 3 described so far has a configuration of a scanning laser microscope, which focuses backscattered light from the observation spot by the objective lens 32, and detects the light by the photodetector 34 by way of the filter 33. When detecting scattered light as such, the transmission wavelength region of the filter 33 is set so as to cover the wavelength of irradiating laser light. An optical pickup device, a scanning laser opthalmoscope, and the like can also be realized with the same configuration. Scanning the light source device 1 may be performed instead of scanning the subject 8. In a scanning laser opthalmoscope, scanning the light source device 1 is often performed. A scanning two-photon microscope can also be realized with almost the same configuration, and in this case, the transmission wavelength region of the filter 33 is set so as to transmit a ½ wavelength component with respect to the irradiated laser wavelength. Moreover, the observing device 3 described so far is of an epi-illumination type, however, an observing device of a transmissive illumination type can also be realized by adopting a configuration that an objective lens for irradiation and an objective lens for detection are arranged to face each other across an subject. The light source device 2 may be used in place of the light source device 1.

Figure 7:
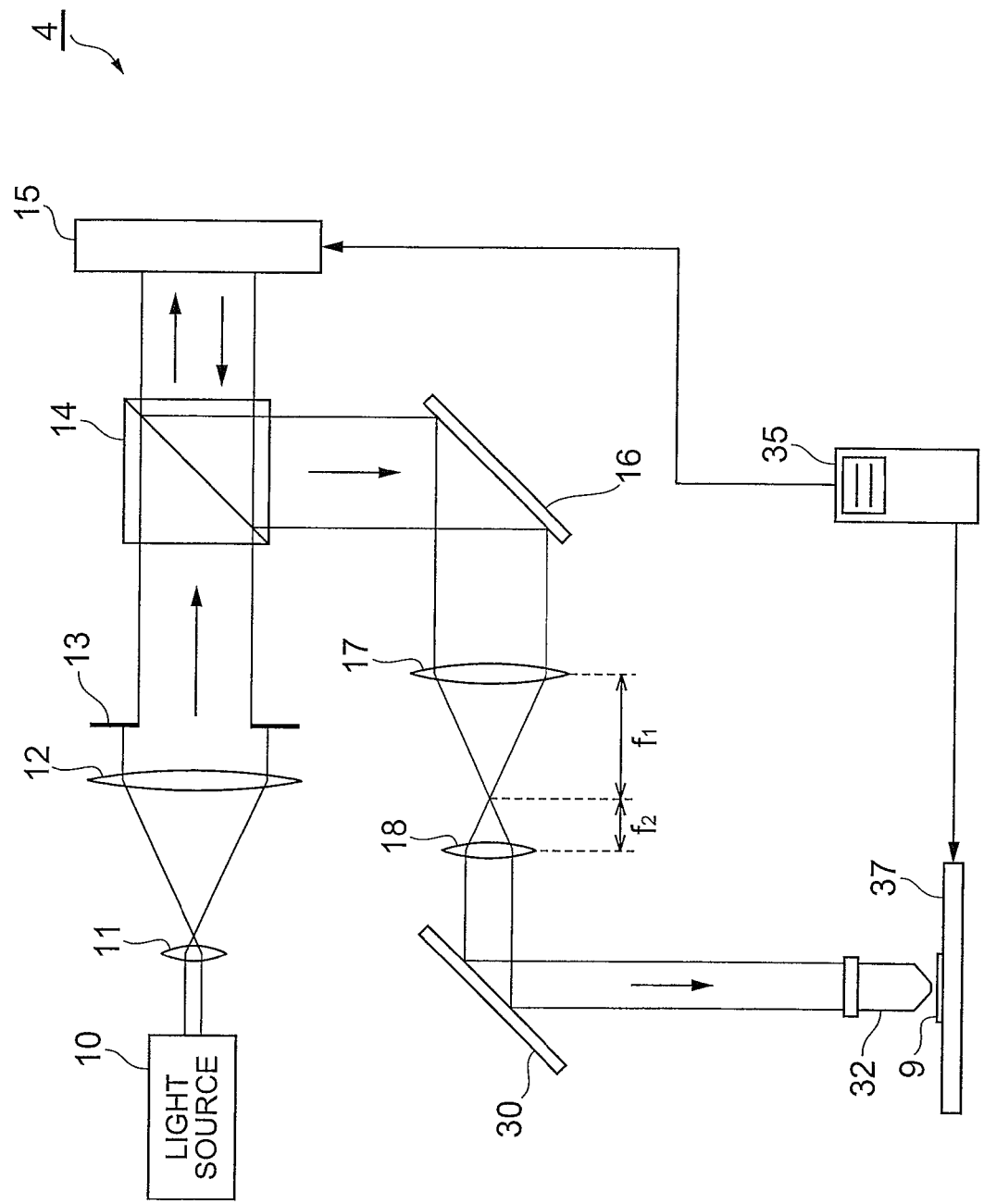
FIG. 7 A configuration diagram of a processing device 4 according to the present embodiment.

Next, description will be given of an embodiment of a processing device according to the present invention. FIG. 7 is a configuration diagram of a processing device 4 according to the present embodiment. The processing device 4 shown in this figure is a device for processing a workpiece 9, and further includes a mirror 30, an objective lens 32, a control unit 35, and a moving stage 37, besides the configuration of the light source device 1 excluding the CCD camera 19 from the configuration shown in FIG. 1.

The mirror 30 reflects light output from the lens 18, and outputs the reflected light to the objective lens 32. The objective lens 32 inputs light propagated from the mirror 30 and focuses and irradiates the light onto a processing spot of the workpiece 9. More specifically, the optical system from the mirror 30 to the objective lens 32 forms an irradiating optical system for focusing and irradiating light output from the light source device 1 onto the processing spot in the workpiece 9.

The control unit 35 moves the moving stage 37 that carries the workpiece 9 to change the position of the processing spot within the workpiece 9. More specifically, the control unit 35 and the moving stage 37 form a scanning unit for scanning the processing spot within the workpiece 9. Moreover, the control unit 35 provides the spatial light modulator 15 with a control signal for setting the amount of phase modulation of each pixel when reflecting light in the spatial light modulator 15 and thereby sets the light intensity distribution in a beam cross section of light output from the light source device 1 as described above.

In the processing device 9, when (p+1) areas sectioned by p circumferences centered on a predetermined position are set on a beam cross section of the light output after being adjusted in beam diameter by the convex lens 17 and the convex lens 18 in the light source device 1, the more outside each of the (p+1) areas is, the wider the radial width of the area is, and the amount of phase modulation is constant in each of the (p+1) areas, and the amounts of phase modulation differ by n between two adjacent areas out of the (p+1) areas. Then, light output from the convex lens 18 is reflected by the mirror 30, and focused and irradiated onto the processing spot within the subject 9 by the objective lens 32. Moreover, the position (processing spot) of focusing and irradiating light from the objective lens 32 onto the workpiece 9 is scanned by the control unit 35 and the moving stage 37.

As described above, when an LG beam having a high-order radial exponent output from the light source device 1 is focused by the objective lens 32, it is impossible to reduce the overall beam diameter smaller than about a half of the wavelength, however, the internal structure of an LG beam is retained. Accordingly, in the processing device 9, the focused spot (processing spot) by the objective lens 32, that is, the central spot (area $A_0$) of an LG mode beam has a size smaller than the diffraction limit. Therefore, providing a scanning step of the workpiece 9 by the moving stage 37 smaller than the size of the central spot (area $A_0$) of an LG beam when being irradiated onto the workpiece 9 allows processing (deforming, breaking, etc.) the workpiece 9 at a very high resolution. It is desirable to drive the moving stage 37 by use of a piezo actuator or the like.

Although light to be focused and irradiated onto a processing spot of the workpiece 9 may be either continuous light or pulsed light, it is necessary to have a sufficient intensity to process the processing point. The light source device 2 may be used in place of the light source device 1.

A light source device according to the present invention is common, and has many applications besides the observing device and processing device described above. For example, a super-resolution effect that can be realized by a Bessel beam as conventionally known can be substituted by the present invention.

Figure 8:
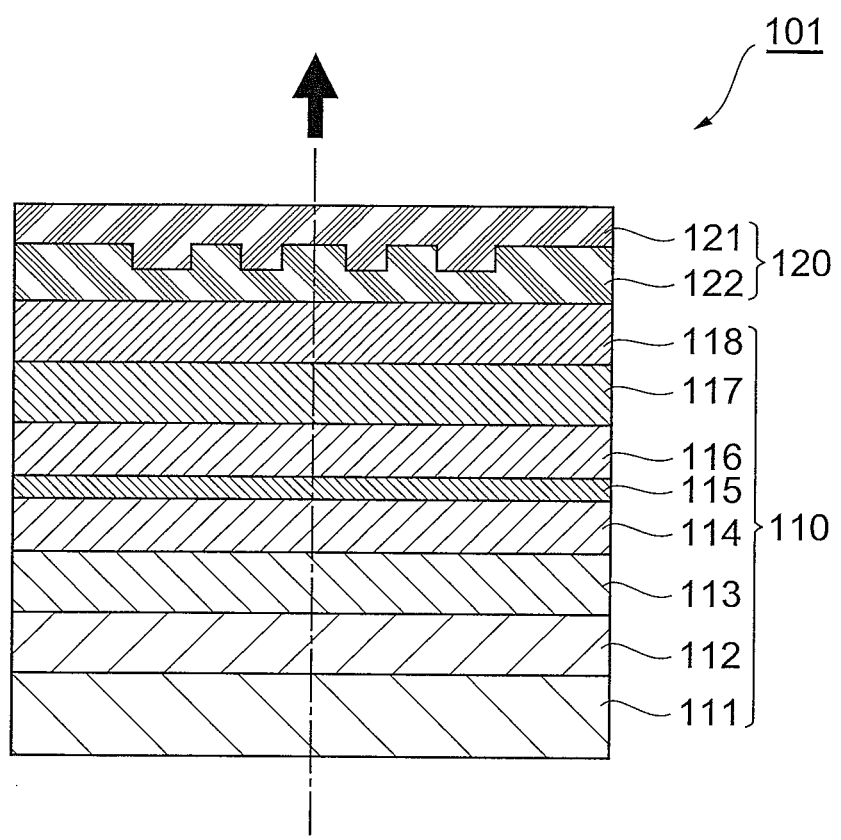
FIG. 8 A sectional view of a light source device 101 according to a third embodiment.
Figure 9:
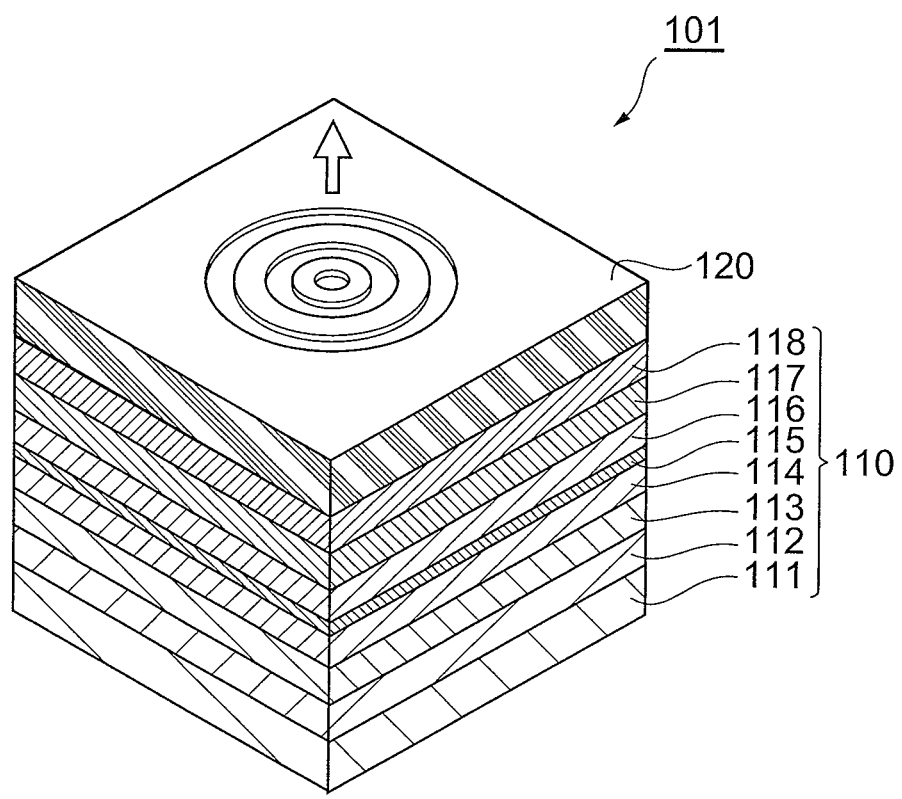
FIG. 9 A perspective view of the light source device 101 according to the third embodiment.

Then, description will be given of a third embodiment of a light source device according to the present invention. FIG. 8 is a sectional view of a light source device 101 according to the third embodiment. FIG. 9 is a perspective view of the light source device 101 according to the third embodiment. The light source device 101 shown in this figure comprises a surface-emitting laser element 110 and a transmissive optical phase-modulation unit 120. The surface-emitting laser element 110 is an example of a light source for outputting coherent light. The optical phase-modulation unit 120 is an example of an optical phase modulator.

The surface-emitting laser element 110 forms a DBR layer 112, a cladding layer 113, a core layer 114, an active layer 115, a core layer 116, a cladding layer 117, and a DBR layer 118 in order on a substrate 111, and a resonator for causing laser oscillation is composed of the DBR layer 112 and the DBR layer 118. The DBR layer 112 on the substrate 111 has high reflectivity at the oscillation wavelength, and the other DBR layer 118 has low reflectivity at the oscillation wavelength.

In the surface-emitting laser element 110, light is emitted in the active layer 115 when a drive current is supplied, and the light reciprocates between the DBR layer 112 and the DBR layer 118, thereby causes an induced emission in the active layer 115, and results in laser oscillation. Then, a part of the light oscillated in the resonator is transmitted through the DBR layer 118 and output from an upper exit surface as laser light.

The optical phase-modulation unit 120 is provided on the exit surface of the surface-emitting laser element 110, transmits and phase-modulates input light according to the position on a beam cross section of the light, and outputs the phase-modulated light. The optical phase-modulation unit 120 is generally realized as a structure in which a plurality of types of media different in refractive index are stacked, and may be realized, with the simplest configuration, as a structure in which two types of media different in refractive index are stacked.

Figure 10:
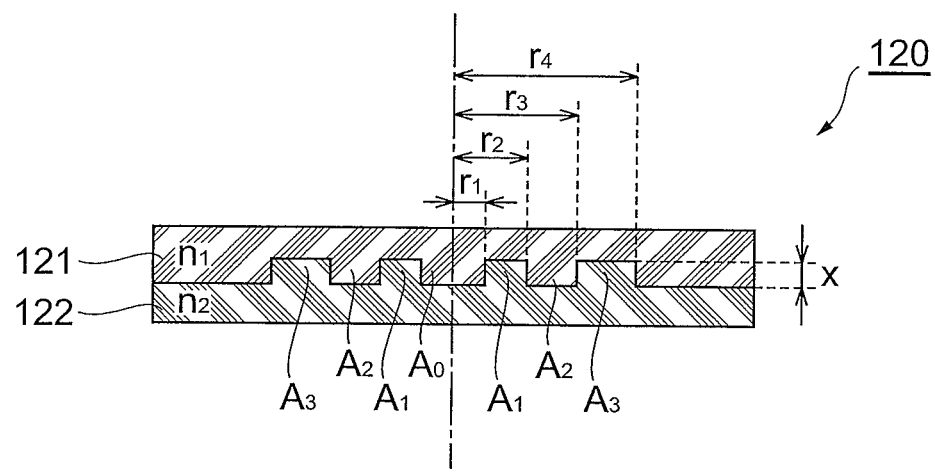
FIG. 10 A sectional view of a transmissive optical phase-modulation unit 120.
Figure 11:
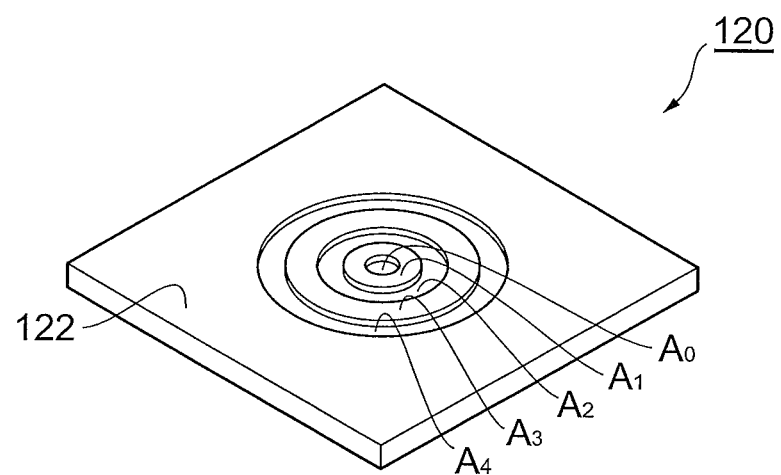
FIG. 11 A perspective view of the transmissive optical phase-modulation unit 120.
Figure 12:
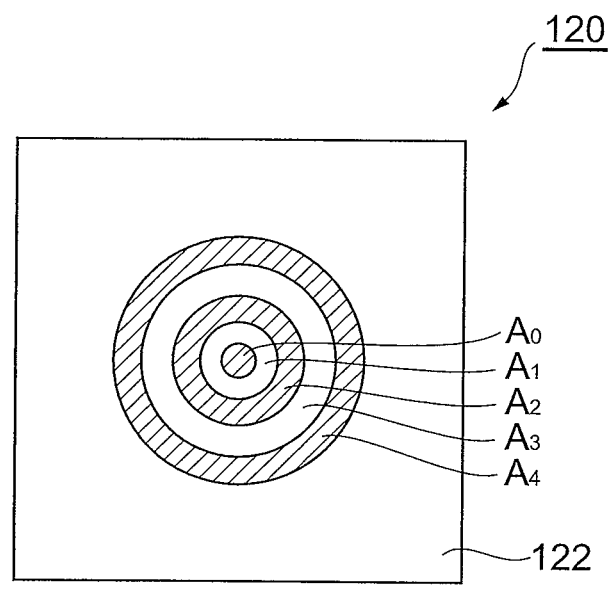
FIG. 12 A plan view of the transmissive optical phase-modulation unit 120.

FIG. 10 is a sectional view of the optical phase-modulation unit 120, FIG. 11 is a perspective view of the optical phase-modulation unit 120, and FIG. 12 is a plan view of the optical phase-modulation unit 120. The optical phase-modulation unit 120 consists of a first medium 121 and a second medium 122 which have mutually different refractive indexes. An upper surface of the first medium 121 and a lower surface of the second medium 122 are parallel to each other. The lower surface of the second medium 122 is in contact with the exit surface of the surface-emitting laser element 110. The first medium 121 and the second medium 122 are made of, for example, a transparent material such as glass or a semiconductor, and may be either gas or vacuum as shown in FIG. 11 and FIG. 12. The hatched areas in FIG. 12 are regions recessed in the second medium 122.

In the optical phase-modulation unit 120, a boundary between the first medium 121 and the second medium 122 has a recessed and projected shape with a step x, and each recess portion and each projection portion at the boundary has a shape of a circular ring or a circle sectioned by a plurality of concentric circles. The step x and the radius $r_1, r_2, r_3, \ldots$ of each of the plurality of concentric circles in the optical phase modulating unit 120 are determined, from a distribution of the amount of phase modulation that needs to be provided for transmission light, as follows. For the sake of simplicity, "$r_0=0$" is defined.

As shown in FIG. 10 to FIG. 12, (p+1) areas $A_0$ to $A_p$ sectioned by p respective circumferences with radii $r_1$ to $r_p$ centered on a predetermined position are set on a beam cross section of light input to the optical phase modulating unit 120. The areas are provided in order from inside as $A_0, A_1, A_2, \ldots, A_p$. The area $A_0$ is an area inside the circumference with a radius $r_1$. The area $A_i$ is an area between the circumference with a radius $r_i$ and the circumference with a radius $r_{i+1}$ (i=1, 2, 3, ..., p−1). The area $A_p$ is an area outside the circumference with a radius $r_p$ and within a light beam (waist radius w).

At this time, the more outside each of the (p+1) areas $A_0$ to $A_p$ is, the wider the radial width of the area. More specifically, the above relational expression (1) holds true between the radii $r_1$ to $r_p$. In addition, the area $A_0$ located at the innermost side has the radius $r_1$ as a radial width thereof.

Further, the amount of phase modulation is constant in each of the (p+1) areas $A_0$ to $A_p$, and the amounts of phase modulation differ by π between two adjacent areas out of the (p+1) areas $A_0$ to $A_p$. More specifically, the amount of phase modulation $\phi_0$ in each area of the even number-th areas $A_0, A_2,$ $A_4, \ldots$ is constant. Also, the amount of phase modulation $\phi_1$ in each area of the odd number-th areas $A_1, A_3, A_5, \ldots$ is constant. In addition, these amounts of phase modulation $\phi_0$ and $\phi_1$ mutually differ by $\pi$.

Lines of phase discontinuity expressed by the p circumferences with radii $r_1$ to $r_p$ that need to be set in terms of the radial direction r are set as follows. The line of phase discontinuity exists at a part (node) where the light intensity equals 0. In the case of an LG mode, the nodes of a light intensity distribution can be determined from zeros of Sonine polynomials. That is, the value of a variable z where a Sonine polynomial $S_p^q(z)$ defined by the above expression (2) takes a value 0 is determined. Here, p, which is referred to as a radial exponent, is a non-negative integer number. In addition, q, which is referred to as an azimuthal exponent, is an arbitrary integer.

In particular, the azimuthal exponent q is provided as a value 0 in the present embodiment. At this time, the above expression (2) results in a Laguerre polynomial expressed by the above expression (3). The Laguerre polynomial is a p-degree polynomial, which has p different positive real roots $a_1$ to $a_p$. By use of these roots $a_i$ and the light beam waist radius w, the radii $r_i$ of the lines of phase discontinuity are expressed by the above expression (4) (i=1, 2, 3, ..., p).

Light transmitted under such phase modulation $\phi(r)$ by the optical phase modulator 120 results in an LG beam having a radial exponent p and an argument exponent 0. The LG beam, with an argument θ in a polar coordinate system set on a phase distribution surface fixed, has a difference in phase value of $\pi$ at points pertaining to two areas that are in contact at a boundary of the line of phase discontinuity. In addition, the more outside each of the (p+1) areas $A_0$ to $A_p$ is, the wider the radial width of the area.

In order to mutually differ the amount of phase modulation $\phi_0$ in each area of the even number-th areas $A_0, A_2, A_4, \ldots$ and the amount of phase modulation $\phi_1$ in each area of the odd number-th areas $A_1, A_3, A_5, \ldots$ by a constant amount $\Delta\phi$, the step x of the recessed and projected shape at the boundary between the first medium 121 and the second medium 122 in the optical phase modulating unit 120 is set to a value expressed by the following expression (5). Here, $n_1$ denotes the refractive index of the first medium 121, $n_2$ denotes the refractive index of the second medium 122, and λ denotes the wavelength of light in a vacuum. In the present embodiment, the step x is determined with "$\Delta\phi=\pi$."

[Numerical Expression 5]

$$x = \frac{\lambda}{2\pi \cdot |n_2 - n_1|} \Delta\phi \quad (5)$$

Light output from the light source device 101 configured as above is an LG beam with a radial exponent p and an azimuthal exponent 0. When such an LG beam having a high-order radial exponent is focused by a lens, it is impossible to reduce the overall beam diameter smaller than about a half of the wavelength (diffraction limit). However, because the internal structure of an LG beam is retained, the central spot (area $A_0$) of a high-order radial exponent LG beam has a size smaller than the diffraction limit on a focused spot.

Rings (siderobes, that is, areas $A_1, A_2, A_3, \ldots$) that exist around the central spot (area $A_0$) exhibit behaviors as in a Bessel beam, and using a technique that has been established in terms of Bessel beams makes it also possible to reduce the influence thereof. As a property unique to a high-order radial exponent LG beam, the greater the radial exponent p is provided, the more the size of the central spot (area $A_0$) can be reduced.

In addition, expansion of the side robes (areas $A_1, A_2, A_3, \ldots$) is theoretically unlimited in Bessel beams, whereas this is limited in a high-order radial exponent LG beam. Therefore, setting an optical system diameter so that the side robes as a whole are completely included therein allows using characteristics of the high-order radial exponent LG beam under more optimal conditions.

Accordingly, the light source device 101 can be suitably used in an observing device for observing an subject at high resolution and a processing device for processing a workpiece at high resolution.

Meanwhile, it can also be considered to apply such a light source device for generating a light beam that can realize a focusing diameter smaller than the diffraction limit to an optical pickup device that performs writing or reading of data with respect to an optical disk capable of recording data at high density.

Conventionally, as beams that can realize focusing diameters smaller than the diffraction limit, zeroth-order Bessel beams have mainly attracted attention. It is known that a zeroth-order Bessel beam is generated by focusing light with an axicon, and the central spot diameter of the Bessel beam is smaller than the diffraction limit. A zeroth-order Bessel beam is also characterized in that the depth of focus in case of focusing is very deep, and has an identical light intensity pattern in a very wide range as compared to that of the depth of focus of a normal beam. This characteristic of a Bessel beam is also called "non-diffraction" propagation, which is desirable when the beam is used for high aspect-ratio processing and the like, however, in the case of reading a multi-layered recording medium, the characteristic is not preferable as this makes focusing control in the depth direction difficult.

Further, in recent years, a radially polarized mode (also inscribed as an R-TEM* mode, which is one of the optical modes with special polarization states) beam has also attracted attention as a light beam that realizes a focusing diameter smaller than the diffraction limit at the time of high-NA focusing (Non-Patent Document 7). However, such a light beam changes in polarization direction depending on the position in the beam, and thus is not suitable for reading of a recording medium using a magneto-optical effect. This is because a linearly polarized or elliptically polarized light source is desired in such case. Further, in a conventional art for generating such a beam, a configuration such as inserting a birefringent medium into a laser medium is necessary, and it is thus inevitable that the device has a large size (Non-Patent Document 8).

Based on the above, in terms of application to an optical pickup device, it can be said that an LG mode beam with an argument exponent 0 has more desirable characteristics than those of other light beams in both aspects of propagation characteristics and polarization characteristics due to focusing. However, because the conventional light source devices for generating LG mode beams are all large-sized, it is difficult to apply the same to optical pickup devices for which downsizing is required.

On the other hand, the light source device 101 according to the third embodiment can be downsized because this is composed of the surface-emitting laser element 110 and the optical phase-modulation unit 120, and therefore, can be suitably used also in an optical pickup device for which a high resolution and downsizing are required.

Figure 13:
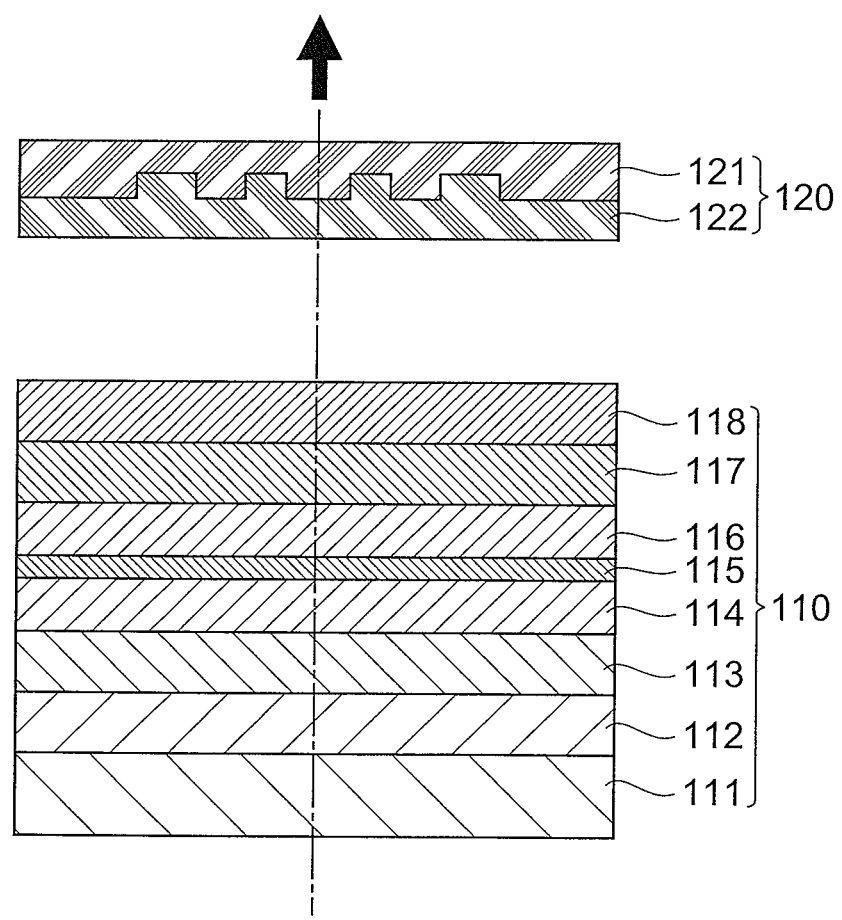
FIG. 13 A sectional view of a light source device according to a modification of the third embodiment.

In addition, the light source device 101 according to the third embodiment described so far includes the surface-emitting laser element 110 and the optical phase-modulation unit 120, where the optical phase-modulation unit 120 is provided on the exit surface of the surface-emitting laser element 110. Here, the exit surface of the surface-emitting laser element 110 may be processed to form the optical phase-modulation unit 120, or alternatively, the separately formed optical phase-modulation unit 120 may be fixed to the exit surface of the surface-emitting laser element 100 as shown in FIG. 13. In the latter case, the optical phase-modulation unit 120 is adhered and fixed to the exit surface of the surface-emitting laser element 110 by, for example, an adhesive.

Figure 14:
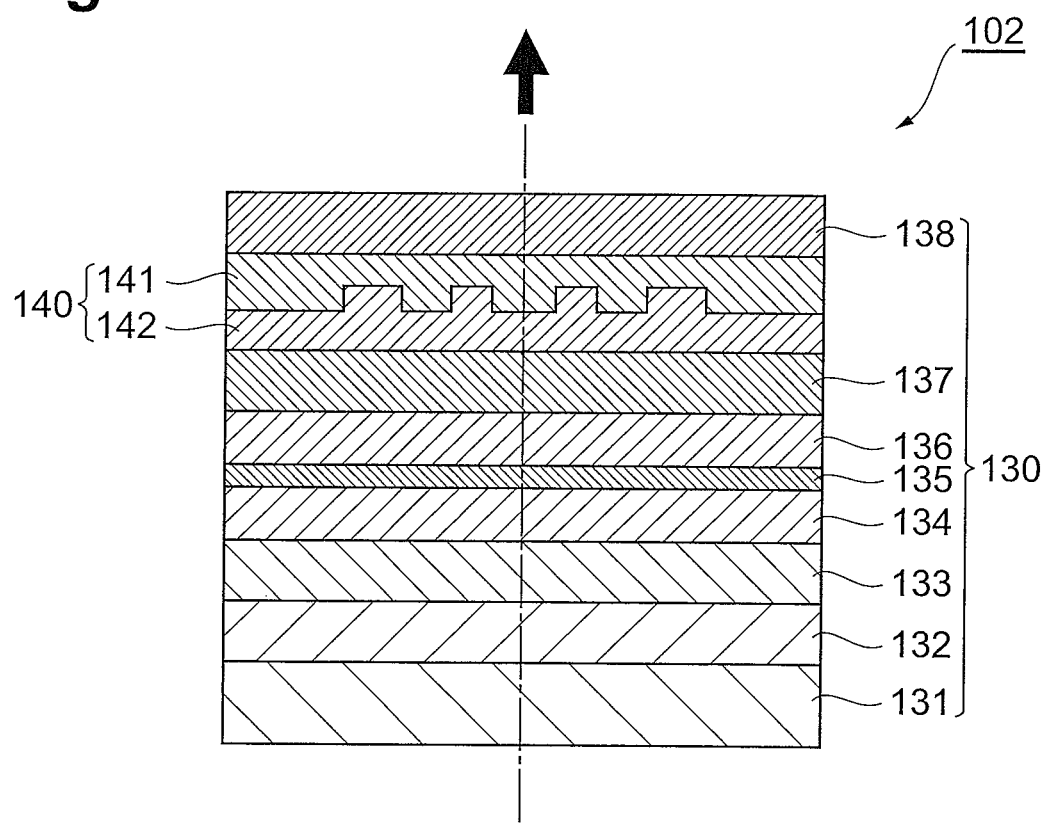
FIG. 14 A sectional view of a light source device 102 according to a fourth embodiment.

Next, description will be given of a fourth embodiment of a light source device according to the present invention. FIG. 14 is a sectional view of a light source device 102 according to a fourth embodiment. The light source device 102 shown in this figure arranges an optical phase modulating unit 140 inside a resonator of a surface-emitting laser element 130.

The surface-emitting laser element 130 forms a DBR layer 132, a cladding layer 133, a core layer 134, an active layer 135, a core layer 136, a cladding layer 137, and a DBR layer 138 in order on a substrate 131, and a resonator for causing laser oscillation is composed of the DBR layer 132 and the DBR layer 138. The DBR layer 132 being on the substrate 131 has high reflectivity at the oscillation wavelength, and the other DBR layer 138 has low reflectivity at the oscillation wavelength.

The optical phase modulating unit 140 is provided between the cladding layer 137 and the DBR layer 138 of the surface-emitting laser element 130. The optical phase-modulation unit 140 is provided within the resonator of the surface-emitting laser element 130, transmits and phase-modulates light propagating in the resonator according to the position on a beam cross section of the light, and outputs the phase-modulated light. The optical phase-modulation unit 140 is generally realized as a structure in which a plurality of types of media different in refractive index are stacked, and may be realized, with the simplest configuration, as a structure for which two types of media different in refractive index are stacked.

The optical phase-modulation unit 140 in the fourth embodiment is the same as the optical phase-modulation unit 120 described with use of FIG. 10 to FIG. 12 in the third embodiment, however the modulation unit 140 is formed inside the surface-emitting laser element 130 and therefore is preferably made of a semiconductor, which is the same material as that of the surface-emitting laser element 130.

In the light source device 102, light is emitted in the active layer 135 when a drive current is supplied, and the light reciprocates between the DBR layer 132 and the DBR layer 138, thereby causes an induced emission in the active layer 135, and results in laser oscillation. In addition, light that is transmitted through the optical phase-modulation unit 140 while the light reciprocates in the resonator undergoes phase modulation during the transmission according to the position on a beam cross section. Then, a part of the light oscillated in the resonator is transmitted through the DBR layer 138 and output from an upper exit surface as laser light.

As a result of the optical phase-modulation unit 140 being set as in the above expressions (1) to (5), light output from the light source device 102 is an LG beam with a radial exponent p and an azimuthal exponent 0. Accordingly, the light source device 102 can also be suitably used in an observing device for observing an subject at high resolution and a processing device for processing a workpiece at high resolution. Moreover, the light source device 102 can also be downsized because this is composed of the surface-emitting laser element 130 and the optical phase-modulation unit 140, and therefore, can be suitably used also in an optical pickup device for which a high resolution and downsizing are required.

Figure 15:
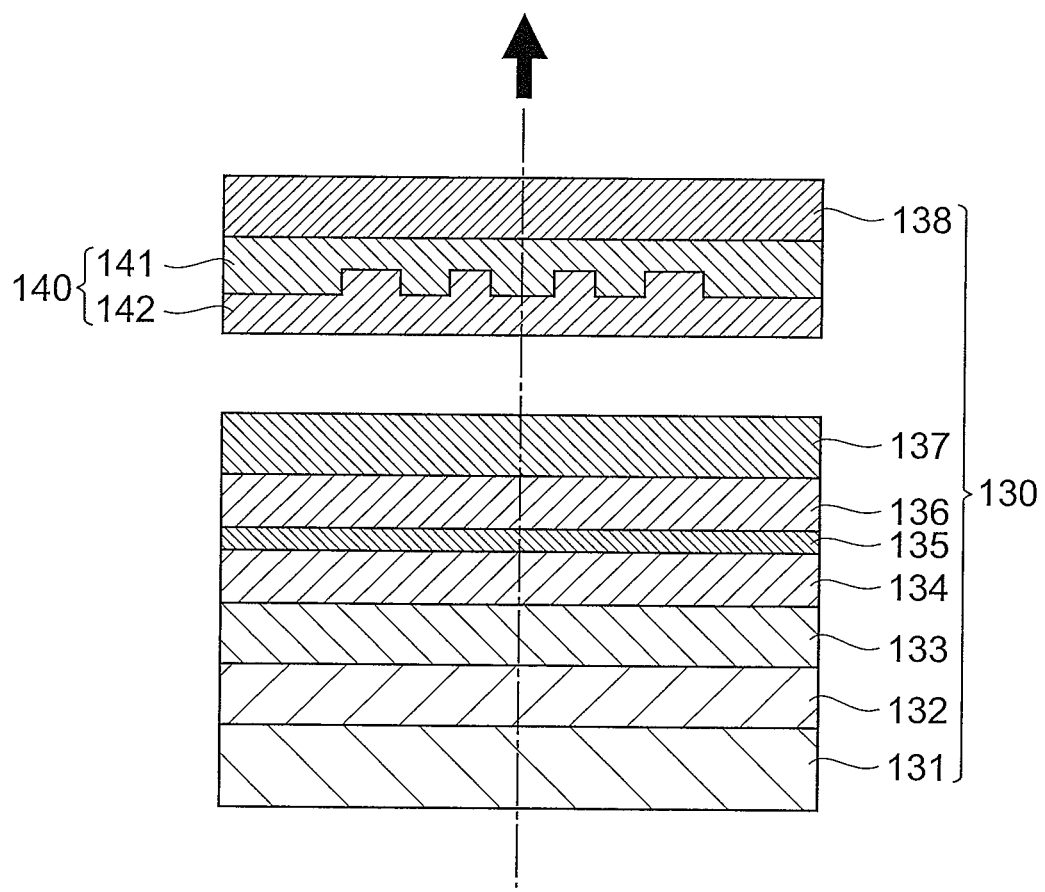
FIG. 15 A sectional view of a light source device according to a modification of the fourth embodiment.

In addition, the light source device 102 according to the fourth embodiment described so far includes the optical phase-modulation unit 140 in the resonator of the surface-emitting laser element 130. Here, the optical phase-modulation unit 140 may be integrally formed in the middle of the manufacturing process of the surface-emitting laser element 130, or alternatively, the separately formed optical phase-modulation unit 140 and DBR layer 138 may be fixed to the surface-emitting laser element 130 (where the DBR layer 138 is excluded) as shown in FIG. 15. In the latter case, the optical phase-modulation unit 140 is adhered and fixed to the cladding layer 137 of the surface-emitting laser element 130 by, for example, an adhesive.

Figure 16:
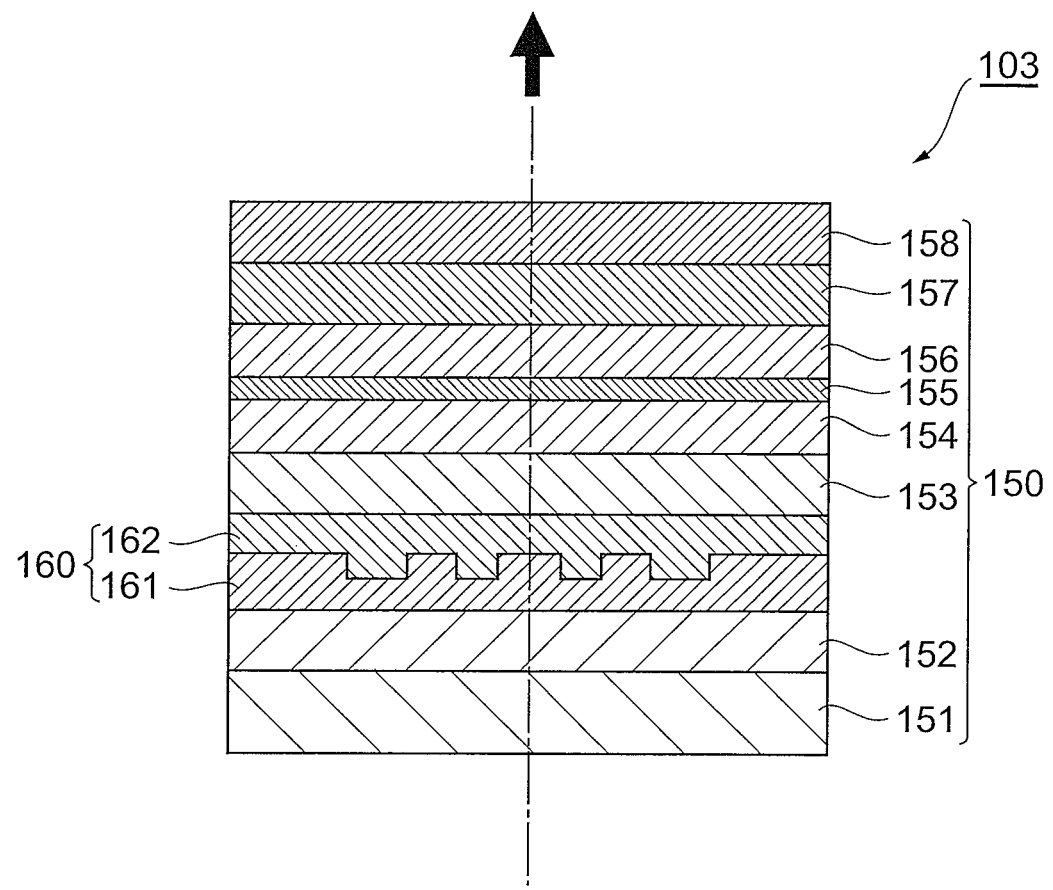
FIG. 16 A sectional view of a light source device 103 according to a fifth embodiment.

Next, description will be given of a fifth embodiment of a light source device according to the present invention. FIG. 16 is a sectional view of a light source device 103 according to a fifth embodiment. For the light source device 103 shown in this figure, an optical phase-modulation unit 160 is provided inside a resonator of a surface-emitting laser element 150.

The surface-emitting laser element 150 forms a DBR layer 152, a cladding layer 153, a core layer 154, an active layer 155, a core layer 156, a cladding layer 157, and a DBR layer 158 in order on a substrate 151, and a resonator for causing laser oscillation is composed of the DBR layer 152 and the DBR layer 158. The DBR layer 152 being on the substrate 151 has high reflectivity at the oscillation wavelength, and the other DBR layer 158 has low reflectivity at the oscillation wavelength.

The optical phase-modulation unit 160 is provided between the DBR layer 152 and the cladding layer 153 of the surface-emitting laser element 150. The optical phase-modulation unit 160 is provided within the resonator of the surface-emitting laser element 150, transmits and phase-modulates light propagating in the resonator according to the position on a beam cross section of the light, and outputs the phase-modulated light. The optical phase-modulation unit 160 is generally realized as a structure in which a plurality of types of media different in refractive index are stacked, and may be realized, with the simplest configuration, as a structure for which two types of media different in refractive index are stacked.

The optical phase-modulation unit 160 in the fifth embodiment is the same as the optical phase-modulation unit 120 described with use of FIG. 10 to FIG. 12 in the third embodiment, however the modulation unit 160 is formed inside the surface-emitting laser element 150 and therefore is preferably made of a semiconductor, which is the same material as that of the surface-emitting semiconductor 150.

In the light source device 103, light is emitted in the active layer 155 when a drive current is supplied, and the light reciprocates between the DBR layer 152 and the DBR layer 158, thereby causes an induced emission in the active layer 155, and results in laser oscillation. In addition, light that is transmitted through the optical phase-modulation unit 160 while the light reciprocates in the resonator undergoes phase modulation during the transmission according to the position on a beam cross section. Then, a part of the light oscillated in the resonator is transmitted through the DBR layer 158 and output from an upper exit surface as laser light.

As a result of the optical phase-modulation unit 160 being set as in the above expressions (1) to (5), light output from the light source device 103 is an LG mode beam with a radial exponent p and an azimuthal exponent 0. Accordingly, the light source device 103 can also be suitably used in an observing device for observing a subject at high resolution and a processing device for processing a workpiece at high resolution. Moreover, the light source device 103 can also be downsized because this is composed of the surface-emitting laser element 150 and the optical phase-modulation unit 160, and therefore, can be suitably used also in an optical pickup device for which a high resolution and downsizing are required.

Figure 17:
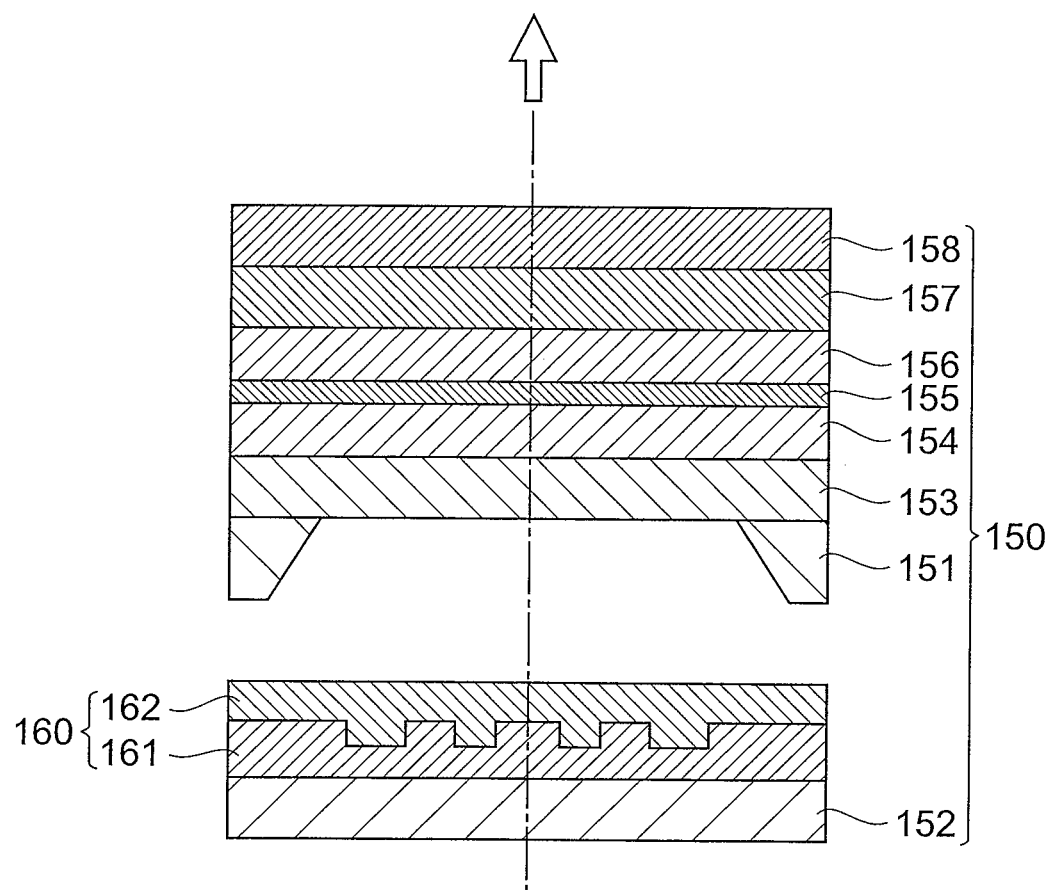
FIG. 17 A sectional view of a light source device according to a modification of the fifth embodiment.

In addition, the light source device 103 according to the fifth embodiment described so far includes the optical phase-modulation unit 160 within the resonator of the surface-emitting laser element 150. Here, the optical phase-modulation unit 160 may be integrally formed in the middle of the manufacturing process of the surface-emitting laser element 150, or alternatively, the separately formed optical phase-modulation unit 160 and DBR layer 152 may be fixed to the surface-emitting laser element 150 (where the DBR layer 152 is excluded) as shown in FIG. 17. In the latter case, the optical phase-modulation unit 160 is adhered and fixed to the cladding layer 153 or the substrate 151 of the surface-emitting laser element 150 by, for example, an adhesive. Moreover, in the latter case, the substrate 151 may be ground to be thin-walled or an opening may be provided in a part of the substrate 151.

(Modification)

The present invention is by no means limited to the above-mentioned embodiments, and can be variously modified. For example, the optical phase modulating unit, which provides phase modulation to transmitted light in the above-mentioned embodiments, may provide phase modulation to reflected light. Such a reflective optical phase modulating unit can be used in DBR layers that compose the resonator of a surface-emitting laser element.

Figure 18:
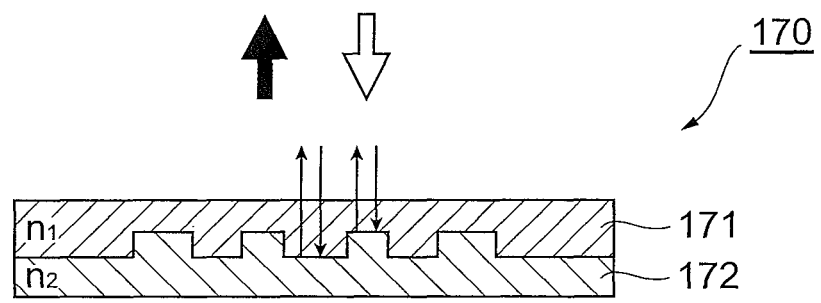
FIG. 18 A sectional view of a reflective optical phase-modulation unit 170.

FIG. 18 is a sectional view of a reflective optical phase-modulation unit 170. The optical phase-modulation unit 170 consists of a first medium 171 and a second medium 172. A boundary between the first medium 171 and the second medium 172 serves as a reflecting surface. The boundary between the first medium 171 and the second medium 172 has a recessed and projected shape with a step x, and each recess portion and each projection portion at the boundary has a shape of a circular ring or a circle sectioned by a plurality of concentric circles. The radius $r_1$, $r_2$, $r_3$, ... of each of the plurality of concentric circles in the optical phase-modulation unit 170 is set as in the above expressions (1) to (4). In terms of where light made incident from the side of the first medium 171 reflects at the boundary, the step x of the recessed and projected shape at the boundary between the first medium 171 and the second medium 172 is set to a value expressed by the following expression (6) in order to mutually differ the amounts of phase modulation between the adjacent areas by a constant amount $\Delta\phi$. Here, $n_1$ denotes the refractive index of the first medium 171, $n_2$ denotes the refractive index of the second medium 172, and $\lambda$ denotes the wavelength of light in a vacuum. The step x is determined with "$\Delta\phi=\pi$."

[Numerical Expression 6]

$$x = \frac{\lambda}{4\pi \cdot n_1}\Delta\phi \quad (6)$$

Figure 19:
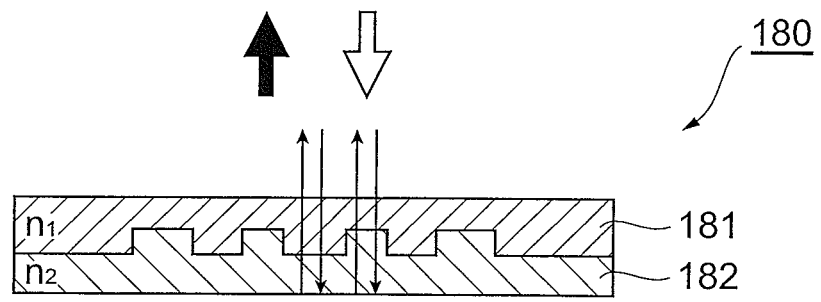
FIG. 19 A sectional view of a reflective optical phase-modulation unit 180.

FIG. 19 is a sectional view of a reflective optical phase modulating unit 180. The optical phase modulating unit 180 consists of a first medium 181 and a second medium 182. A lower surface of the second medium 182 serves as a reflecting surface. The lower surface of the second medium 182 is preferably applied with reflection coating. The boundary between the first medium 181 and the second medium 182 has a recessed and projected shape with a step x, and each recess portion and each projection portion at the boundary has a shape of a circular ring or a circle sectioned by a plurality of concentric circles. The radius $r_1$, $r_2$, $r_3$, ... of each of the plurality of concentric circles in the optical phase modulating unit 180 is set as in the above expressions (1) to (4). In terms of where light made incident from the side of the first medium 181 reflects at the boundary, the step x of the recessed and projected shape at the boundary between the first medium 181 and the second medium 182 in the optical phase modulating unit 180 is set to a value expressed by the following expression (7) in order to mutually differ the amounts of phase modulation between the adjacent areas by a constant amount $\Delta\phi$. Here, $n_1$ denotes the refractive index of the first medium 181, $n_2$ denotes the refractive index of the second medium 182, and $\lambda$ denotes the wavelength of light in a vacuum. The step x is determined with "$\Delta\phi=\pi$."

[Numerical Expression 7]

$$x = \frac{\lambda}{4\pi \cdot |n_2 - n_1|}\Delta\phi \quad (7)$$

Example

Figure 20:
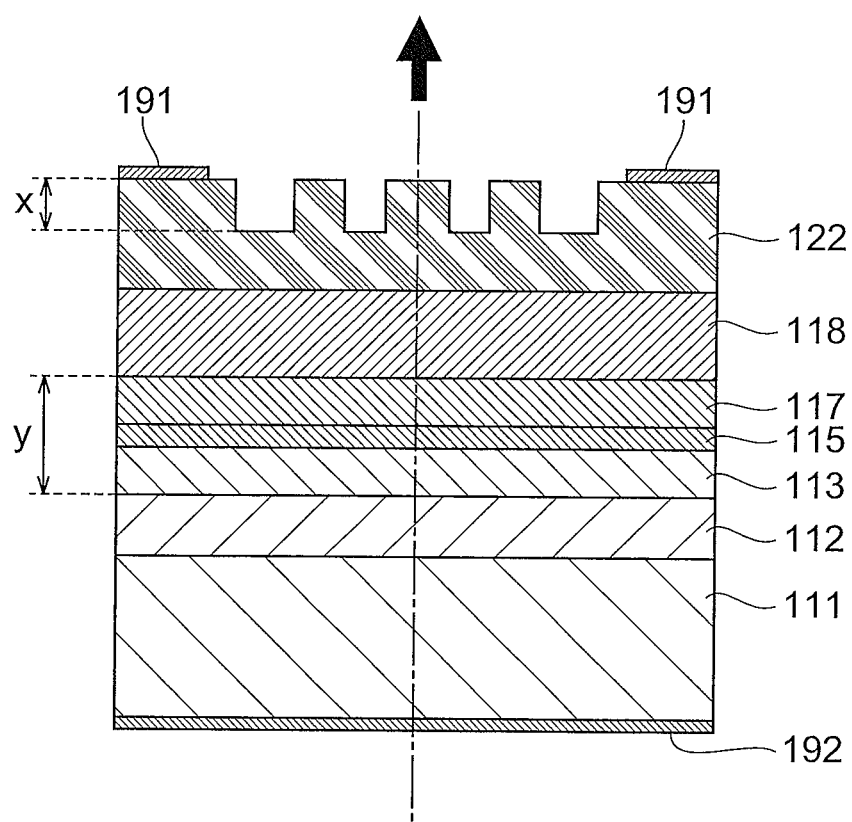
FIG. 20 A sectional view of a light source device of the present example.

Next, description will be given of a light source device of an example. FIG. 20 is a sectional view of a light source device of the present example. The light source device of the present example is corresponding to a modification of the configuration of the third embodiment in the above. In the light source device of the present example, the first medium 121 of the optical phase modulating unit 120 is air, and a p-electrode 191 is provided on the second medium 122 of the optical phase-modulation unit 120, and an n-electrode 192 is provided on the back surface of the substrate 111. Moreover, no core layers 114 and 116 are provided.

The substrate 111 is made from n$^+$-GaAs. For the DBR layer 112, n$^-$-GaAs (68 nm thick) and n$^-$-AlAs (82 nm thick) are alternately stacked, and the number of layers of each is 20. The cladding layer 113 is made from n$^-$-Al$_{0.45}$Ga$_{0.55}$As (71.5 nm thick). The active layer 115 is made from In$_{0.2}$Ga$_{0.8}$As (8 nm thick). The cladding layer 117 is made from p$^-$-Al$_{0.45}$Ga$_{0.55}$As (71.5 nm thick). For the DBR layer 118, p$^-$-GaAs (68 nm thick) and p$^-$-AlAs (82 nm thick) are alternately stacked, and the number of layers of each is 20. The second medium 122 is made from p$^+$-GaAs (400 nm thick).

The p-electrode 191 is made of a multiple metal layer of Cr (50 nm thick)/Au (150 nm thick), and provided on the front surface of the second medium 122 of the optical phase-modulation unit 120, and particularly provided in a ring shape at the outermost area of the front surface of the second medium 122 formed in a recessed and projected shape. The n-electrode 192 is made of a multiple metal layer of Au (100 nm thick)/AuGe (150 nm thick)/Ni (50 nm thick), and provided substantially over the rear surface of the substrate 111.

The front surface of the second medium 122 of the optical phase-modulation unit 120 has a recessed and projected shape with a step x, and each recess portion and each projection portion at the boundary has a shape of a circular ring or a circle sectioned by a plurality of concentric circles. The radius of each of the plurality of concentric circles and the step x are determined as described above. The second medium 122 of the optical phase-modulation unit 120 has a refractive index of 3.5, and the step x is provided as 196 nm.

The interval between the DBR layer 112 and the DBR layer 118 (that is, the cavity length of the resonator) y is determined based on the refractive index and oscillation wavelength therebetween. The cladding layers 113 and 117 each have a refractive index of 3.25, and the interval y is provided as 151 nm. Moreover, in each of the DBR layers 112 and 118, the thickness of each of the GaAs and AlAs layers is set so that the Bragg reflection wavelength equals the oscillation wavelength.

In the light source device of the present example thus configured, when a drive current is supplied between the electrode 191 and the electrode 192, light is emitted in the active layer 115, and the light reciprocates between the DBR layer 112 and the DBR layer 118, and thereby causes an induced emission in the active layer 115 and results in laser oscillation. Then, a part of the light oscillated in the resonator is transmitted through the DBR layer 118 and output from an upper exit surface as laser light with a wavelength of 890 nm. The laser light undergoes phase modulation by the second medium 122 of the optical phase-modulation unit 120 according to the position on a beam cross section, and is output as an LG beam with an azimuthal exponent 0.

The invention claimed is:

1. A light source device comprising:
a light source for outputting coherent light; and
an optical phase modulator for inputting the light output from the light source, phase-modulating the light according to a position on a beam cross section of the light, and outputting the phase-modulated light,
wherein when (p+1) areas sectioned by p circumferences centered on a predetermined position are set on a beam cross section of the light input to the optical phase modulator, p being a natural number and being greater than or equal to 2, the more outside each of the (p+1) areas is, the wider the radial width of the area, an amount of phase modulation is constant in each of the (p+1) areas, and the amounts of phase modulation differ by t between two adjacent areas out of the (p+1) areas, and
wherein the radial width is defined as a difference between radii of an exterior border and an interior border of a respective area.

2. A light source device comprising:
a light source for outputting coherent light; and
an optical phase modulator for inputting the light output from the light source, phase-modulating the light according to a position on a beam cross section of the light, and outputting the phase-modulated light, wherein an amount of phase modulation in each pixel is set based on an externally input control signal for the optical phase modulator,
wherein when (p+1) areas sectioned by p circumferences centered on a predetermined position are set on a beam cross section of the light input to the optical phase modulator, p being a natural number and being greater than or equal to 2, the more outside each of the (p+1) areas is, the wider the radial width of the area, the amount of phase modulation is constant in each of the (p+1) areas, and the amounts of phase modulation differ by $\pi$ between two adjacent areas out of the (p+1) areas, and
wherein the radial width is defined as a difference between radii of an exterior border and an interior border of a respective area.

3. An observing device for observing a subject, the observing device comprising:
the light source device according to claim 2;
an irradiating optical system for focusing and irradiating light output from the light source device onto an observation spot within the subject,
a scanning unit for scanning the observation spot within the subject, and
a detecting optical system for detecting light generated as a result of focusing and irradiating light onto the observation spot by the irradiating optical system.

4. A processing device for processing a workpiece, the processing device comprising:
the light source device according to claim 2;
an irradiating optical system for focusing and irradiating light output from the light source device onto a processing spot within the workpiece; and
a scanning unit for scanning the processing spot within the workpiece.

* * * * *

UNITED STATES PATENT AND TRADEMARK OFFICE
CERTIFICATE OF CORRECTION

PATENT NO. : 8,553,733 B2  Page 1 of 1
APPLICATION NO. : 12/527618
DATED : October 8, 2013
INVENTOR(S) : Ando et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 598 days.

Signed and Sealed this
Fifteenth Day of September, 2015

Michelle K. Lee
*Director of the United States Patent and Trademark Office*